United States Patent
Dejima et al.

(10) Patent No.: US 9,826,887 B2
(45) Date of Patent: *Nov. 28, 2017

(54) SURGICAL DEVICE, OUTER TUBE, ENDOSCOPE, AND TREATMENT TOOL

(71) Applicant: FUJIFILM Corporation, Tokyo (JP)

(72) Inventors: Takumi Dejima, Kanagawa (JP); Masayuki Iwasaka, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/864,887

(22) Filed: Sep. 25, 2015

(65) Prior Publication Data

US 2016/0029876 A1 Feb. 4, 2016

Related U.S. Application Data

(63) Continuation of application No. PCT/JP2014/058776, filed on Mar. 27, 2014.

(30) Foreign Application Priority Data

Mar. 29, 2013 (JP) .................................. 2013-074012

(51) Int. Cl.
*A61B 1/00* (2006.01)

(52) U.S. Cl.
CPC ...... *A61B 1/00154* (2013.01); *A61B 1/00087* (2013.01)

(58) Field of Classification Search
CPC .......................... A61B 1/00154; A61B 1/00087
(Continued)

(56) References Cited

U.S. PATENT DOCUMENTS 4,610,242 A * 9/1986 Santangelo ............ A61B 17/34
 600/114
4,927,827 A * 5/1990 Katoh .................. C07D 401/04
 514/256

(Continued)

FOREIGN PATENT DOCUMENTS

JP 08-140988 6/1996
JP 08-164148 6/1996

(Continued)

OTHER PUBLICATIONS

"Written Opinion of the International Searching Authority" of PCT/JP2014/058776, mailed on Jun. 24, 2014, with English translation thereof, pp. 1-12, in which the listed references (Ref.1-6) were cited.

(Continued)

*Primary Examiner* — Pedro Philogene
*Assistant Examiner* — David C Comstock
(74) *Attorney, Agent, or Firm* — JCIPRNET

(57) ABSTRACT

A surgical device, an outer tube, an endoscope, and a treatment tool that have a simple configuration and excellent operability are provided. The outer tube includes a slider in an outer tube body. When the endoscope and the treatment tool are inserted into the outer tube, the endoscope and treatment tool are held by an endoscope holding part and a treatment tool holding part each being provided in the slider so as to be integrated. When the treatment tool is moved in the axial direction, the endoscope is moved in the axial direction in interlock with the movement. In the outer tube, the opening type hermetic valve part for the endoscope in a valve member has the inner diameter larger than the inner diameter of the elastic member for causing the endoscope holding part to hold the endoscope.

24 Claims, 21 Drawing Sheets

(58) Field of Classification Search
USPC ....... 600/203, 208, 227, 104, 109, 114, 121, 600/122, 128, 129, 160; 606/191
See application file for complete search history.

(56) References Cited

U.S. PATENT DOCUMENTS

| | | | |
|---|---|---|---|
| 5,836,869 A | 11/1998 | Kudo et al. | |
| 5,879,287 A * | 3/1999 | Yoshihashi | A61B 1/00142 600/121 |
| 6,036,637 A | 3/2000 | Kudo | |
| 6,162,236 A | 12/2000 | Osada | |
| 2005/0096695 A1 | 5/2005 | Olich | |
| 2005/0119525 A1 | 6/2005 | Takemoto | |
| 2005/0234297 A1 | 10/2005 | Devierre et al. | |
| 2007/0106118 A1 | 5/2007 | Moriyama | |
| 2007/0232863 A1 | 10/2007 | Miyake et al. | |
| 2007/0265502 A1 | 11/2007 | Minosawa et al. | |
| 2010/0105983 A1 | 4/2010 | Oneda et al. | |
| 2011/0257671 A1 | 10/2011 | Trovato et al. | |
| 2013/0012783 A1 | 1/2013 | Vayser et al. | |
| 2015/0080650 A1 | 3/2015 | Dejima et al. | |
| 2016/0022122 A1 * | 1/2016 | Dejima | A61B 1/00087 600/210 |
| 2016/0051280 A1 * | 2/2016 | Dejima | A61B 1/00087 600/114 |

FOREIGN PATENT DOCUMENTS

| | | |
|---|---|---|
| JP | 10-118076 | 5/1998 |
| JP | 11-342107 | 12/1999 |
| JP | 2004-041580 | 2/2004 |
| JP | 2004180858 | 7/2004 |
| JP | 2005152416 | 6/2005 |
| JP | 2006-014960 | 1/2006 |
| JP | 2007222239 | 9/2007 |
| JP | 2007301378 | 11/2007 |
| WO | 2006129440 | 12/2006 |
| WO | 2013176167 | 11/2013 |

OTHER PUBLICATIONS

"Office Action of Japanese Related Application No. 2015-508670", with English translation thereof, issued on Aug. 29, 2016, p. 1-7.
"Written Opinion of the International Searching Authority of PCT/JP2014/058775", this report contains the following items: Form PCT/ISA237(cover sheet), PCT/ISA237(Box No. I),PCT/ISA237(Box No. V), PCT/ISA237(Box No. VI) and PCT/ISA237(Box No. VIII), mailed on May 20, 2014, which is English translation of "Written Opinion of the International Searching Authority", pp. 1-10.
"Written Opinion of the International Searching Authority of PCT/JP2014/058777", this report contains the following items: Form PCT/ISA237 (cover sheet), PCT/ISA237 (Box No. I), PCT/ISA237 (Box No. V), PCT/ISA237 (Box No. VI) and PCT/ISA237 (Box No. VIII), mailed on May 20, 2014, with English translation thereof, pp. 1-11.
"Office Action of US Counterpart Application," dated Jul. 20, 2017, p1-p52.

* cited by examiner

SURGICAL DEVICE, OUTER TUBE, ENDOSCOPE, AND TREATMENT TOOL

CROSS-REFERENCE TO RELATED APPLICATIONS

This application is a Continuation of PCT International Application No. PCT/JP2014/058776 filed on Mar. 27, 2014, which claims priority under 35 U.S.C. §119(a) to Japanese Patent Application No. 2013-074012 filed on Mar. 29, 2013. Each of the above application(s) is hereby expressly incorporated by reference, in its entirety, into the present application.

BACKGROUND OF THE INVENTION

Field of the Invention

The present invention relates to a surgical device that uses an outer tube to guide multiple medical instruments (e.g., an endoscope and a treatment tool) into a body cavity.

Description of the Related Art

A laparoscope has been known as an endoscopic instrument that is inserted from the skin on a body surface into an abdominal cavity. A surgery (laparoscopic surgery) using this laparoscope only requires a smaller surgical wound than laparotomy and thoracotomy do, and can reduce the post-operation bed rest period. Consequently, such a surgery has recently been widespread in many operations.

Typically, in a laparoscopic surgery (e.g., laparoscopic cholecystectomy etc.), an operator who performs treatment and a laparoscopist who operates a laparoscope are present. The treatment and the operation of the laparoscope are separately performed. Consequently, during the operation, the operator performs treatment while successively instructing the laparoscopist in order to obtain an optimal image for treatment.

However, according to the scheme where the operator instructs the laparoscopist, it is difficult to obtain an image which the operator actually wishes, thereby causing a problem in that stress is applied to the operator. Furthermore, the laparoscopist performs an operation after the operator issues an instruction, thereby causing another problem in that the operation requires time. Moreover, a hand of the operator and a hand of the laparoscopist sometimes interfere with each other above the abdominal wall of a patient, thereby causing yet another problem in that the operation becomes complicated.

Japanese Patent Application Laid-Open No. 2007-301378 (PTL 1) describes a technique as a configuration that allows a treatment tool and an endoscope to move in interlock with each other. The technique detects the amount of insertion and inclination of the treatment tool, controls optical zooming and electronic zooming of the endoscope to cause the imaging range of the endoscope to follow the movement of the treatment tool.

Furthermore, Japanese Patent Application Laid-Open No. 10-118076 (PTL 2) and Japanese Patent Application Laid-Open No. 2007-222239 (PTL 3) describe a technique that provides a marker at a distal end part of a treatment tool, detects the position of the marker to thereby detect the position of the treatment tool, and causes the imaging range of the endoscope to follow the movement of the treatment tool.

Moreover, Japanese Patent Application Laid-Open No. 8-164148 (PTL 4) describes a technique that causes a magnetic sensor provided for a treatment tool to detect the position of the treatment tool, and allows the imaging range of an endoscope to follow the movement of the treatment tool.

SUMMARY OF THE INVENTION

However, the method that detects the position or the like of the treatment tool and causes the imaging range of the endoscope to follow the movement of the treatment tool as with the conventional case has a problem in that the scale of the system becomes large.

The present invention is made in view of such situations, and has an object to provide a surgical device, an outer tube, an endoscope, and a treatment tool that have a simple configuration and achieve high operability.

Solutions to the problem are as follows.

A first aspect is a surgical device including: a first medical instrument that includes an insertion part; a second medical instrument that includes an insertion part; and an outer tube into which the insertion part of the first medical instrument and the insertion part of the second medical instrument are inserted, and is configured to guide the insertion part of the first medical instrument and the insertion part of the second medical instrument into a body cavity, wherein the outer tube comprises: a cylindrical outer tube body into which the insertion part of the first medical instrument and the insertion part of the second medical instrument are inserted; a first entry port provided at a proximal end part of the outer tube body; a second entry port provided at the proximal end part of the outer tube body; a first sealing member which is provided at the first entry port, and configured to slidably seal the insertion part of the first medical instrument; a second sealing member which is provided at the second entry port, and configured to slidably seal the insertion part of the second medical instrument; a first exit port provided at a distal end part of the outer tube body; a second exit port provided at the distal end part of the outer tube body; a movable object which is arranged in the outer tube body and is configured to be movable in the outer tube body in an axial direction; a first holding part which is provided at the movable object and configured to hold the insertion part of the first medical instrument inserted into the outer tube body; and a second holding part which is provided at the movable object and configured to hold the insertion part of the second medical instrument inserted into the outer tube body, and the insertion part of the first medical instrument comprises: a part which is to be held by the first holding part and has a first diameter $A1$; and a part which is disposed closer to a proximal end than the part having the first diameter $A1$, and is configured to maintain hermeticity with the first sealing member, and has a second diameter $A2$ being larger than the first diameter $A1$.

According to this aspect, the first medical instrument and the second medical instrument are inserted into the body cavity through the outer tube. The outer tube is configured to include the cylindrical outer tube body and the movable object arranged in the outer tube body. When inserted into the outer tube body, the first medical instrument and the second medical instrument are held by the first holding part and the second holding part provided at the movable object, so as to be integrated. The movable object is configured to be movable along the axis of the outer tube body. When the first medical instrument is moved in the axial direction, the second medical instrument is moved in interlock with the movement. Likewise, when the second medical instrument is moved in the axial direction, the first medical instrument is moved in interlock with the movement. In this case, for example, if the first medical instrument is the endoscope and the second medical instrument is the treatment tool, the endoscope can be moved in interlock with the movement of the treatment tool. This movement allows the visual field (imaging region) of the endoscope to follow the treatment part, thereby allowing the operator to be always provided with an image optimal to treatment. That is, the image desired by the operator can be displayed without stress. Furthermore, the first medical instrument and the second medical instrument are inserted into the body cavity through the outer tube. Consequently, only a single site to be punctured into the body cavity wall is required. Therefore, a low-invasive operation (operation with a small load to the body) can be performed. Note that visual field of the first medical instrument is moved in the forward and rear direction (to-and-fro movement) by movement of the second medical instrument in the axial direction. Meanwhile, the movement in the vertical and horizontal directions is performed by the inclination movement of the second medical instrument. That is, all the parts including the outer tube are inclined to move the visual field. In this case, because the inclination movement of the outer tube can move the visual field, the incision is not required to be enlarged to perform treatment or move the visual field. Therefore, the low-invasive operation can be performed. Typically, laparoscopic surgery is performed where gas is supplied into an abdominal cavity to expand the abdominal cavity. Because the first medical instrument entry port and the second medical instrument entry port, which are provided at the outer tube, respectively have sealing members (the first sealing member and the second sealing member), the hermeticity can be secured.

Further, according to this aspect, the insertion part of the first medical instrument includes: the part which is to be held by the first holding part and has the first diameter A1; and the part which is disposed closer to the proximal end than (on the proximal end side with respect to) the part having the first diameter A1, and is configured to maintain hermeticity with the first sealing member, and has the second diameter A2 larger than the first diameter A1. Consequently, the insertion and extraction operation of the first medical instrument into and from the outer tube can be easily performed. That is, such a configuration can eliminate the sliding friction applied from the first sealing member during insertion and extraction of the first medical instrument at the distal end part side of the first medical instrument. Consequently, the insertion and extraction operation of the first medical instrument can be smoothly performed without unnecessary force. Furthermore, the load applied to the first sealing member can be reduced, and the life-span of the first sealing member can be increased. Moreover, in the first medical instrument, the part exposed from the proximal end part of the outer tube is formed thick. Consequently, the instrument becomes resistant to deformation, and direct operational feeling with high stiffness can be obtained. Furthermore, because the diameter of the first holding part can be reduced, the size of the movable object contained in the outer tube can also be reduced, which can, in turn, reduce the entire size of the outer tube.

Note that it is preferable that the part where the diameter is varied be formed so as to allow the diameter to be smoothly varied.

A second aspect is a mode of the surgical device according to the first aspect, in which the insertion part of the second medical instrument includes: a part which is to be held by the second holding part and has a first diameter B1; and a part which is disposed closer to a proximal end than (on a proximal end side with respect to) the part having the first diameter B1, and is configured to maintain hermeticity with the second sealing member, and has a second diameter B2 being larger than the first diameter B1.

According to this aspect, the second medical instrument is also formed as with the first medical instrument. Consequently, also for the second medical instrument, advantageous functional effects analogous to the effects of the first medical instrument can be achieved.

It is preferable that the second medical instrument be also formed such that the part where the diameter is varied be formed so as to allow the diameter to be smoothly varied.

A third aspect is a mode of the surgical device according to the first or second aspect, in which the first medical instrument is an endoscope.

According to this aspect, the first medical instrument is configured by the endoscope. Consequently, the endoscope can be moved in interlock with the movement of the second medical instrument (e.g., treatment tool), and the image desired by the operator can be displayed without stress.

A fourth aspect, is a mode of the surgical device according to the third aspect, in which the endoscope internally includes an imaging device (imaging means) at a distal end of the insertion part.

According to the surgical device of this aspect, the endoscope internally includes the imaging means at the distal end of the insertion part.

A fifth aspect is a mode of the surgical device of the first or second aspect, in which the first medical instrument is a treatment tool.

According to this aspect, the first medical instrument is configured by the treatment tool. Consequently, the second medical instrument (e.g., endoscope) can be moved in interlock with the movement of the treatment tool.

A sixth aspect is a mode of the surgical device of any one of the first to fifth aspects, wherein the first holding part can adjust a holding position of the insertion part of the first medical instrument.

According to this aspect, the position of the insertion part of the first medical instrument held by the first holding part can be adjusted in the axial direction. Consequently, it is possible to adjust the relative positional relationship (the positional relationship of the distal end) between the first medical instrument and the second medical instrument that are connected via the movable object. Accordingly, for example, if the first medical instrument or the second medical instrument is configured by an endoscope, the imaging range can be adjusted and the usability can be improved.

A seventh aspect is a mode of the surgical device of any one of the first to sixth aspects, wherein the second holding part can adjust a holding position of the insertion part of the second medical instrument.

According to this aspect, the position of the insertion part of the second medical instrument held by the second holding part can be adjusted in the axial direction. Consequently, it is possible to adjust the relative positional relationship (the positional relationship of the distal end) between the first medical instrument and the second medical instrument that are connected via the movable object. Accordingly, for example, if the first medical instrument or the second medical instrument is configured by an endoscope, the imaging range can be adjusted and the usability can be improved.

An eighth aspect is a mode of the surgical device according to any one of the first to seventh aspects, wherein the first sealing member has a hole and is configured by a plate-shaped elastic body, the first holding part includes an annular elastic member through which the insertion part of the first medical instrument is inserted, and the hole of the first sealing member is configured to have a diameter that is larger than an inner diameter of the elastic member of the first holding part.

According to this aspect, the first sealing member is configured by the plate-shaped elastic body, and is provided with the hole into which the first medical instrument is inserted. If the insertion part of the first medical instrument is inserted into the hole, the gap formed between the first entry port is sealed. According to this aspect, the first holding part includes an annular elastic member, and the insertion part of the first medical instrument is inserted into the annular elastic member, thereby holding the first medical instrument. Consequently, the position of the insertion part of the first medical instrument held by the first holding part can be adjusted in the axial direction. According to this aspect, in the outer tube, the diameter of the hole which is provided at the first sealing member is configured to be larger than the inner diameter of the elastic member of the first holding part. Consequently, the insertion and extraction operation of the first medical instrument for the outer tube can be easily performed.

A ninth aspect is a mode of the surgical device of any one of the first to eighth aspects, wherein the movable object includes: a movable object main body configured to be movable with respect to the outer tube body in the axial direction; and a movable part configured to be movable with respect to the movable object main body in the axial direction, and one of the first holding part and the second holding part is provided in the movable part, and another one of the first holding part and the second holding part is provided in the movable object main body.

According to this aspect, the movable object is configured to include the movable object main body configured to be movable in the axial direction with respect to the outer tube body, and the movable part configured to be movable in the axial direction with respect to the movable object main body. And, one of the first holding part and the second holding part is provided in the movable part, and another one of the first holding part and the second holding part is provided in the movable object main body. Consequently, interlocked movement of the first medical instrument and the second medical instrument can have "play (non-sensitive region)". That is, within a predetermined range (movable range), the movement of the first medical instrument can be prevented from being transmitted to the second medical instrument (the movement of the second medical instrument can be prevented from being transmitted to the first medical instrument). Such interlocked movement of the first medical instrument and the second medical instrument is thus provided with "play". Consequently, for example, in the case where the first medical instrument is configured by an endoscope, minute movement of the second medical instrument in the axial direction (to-and-fro movement with a small amplitude and the like) can be prevented from being transmitted to the endoscope. Therefore, the image on the screen can be prevented from swaying due to minute movement of the second medical instrument. An easily viewable image can be always provided for the operator.

A tenth aspect is a mode of the surgical device of the ninth aspect, wherein the movable object main body is configured to have a greater movement resistance to the outer tube body than a movement resistance of the movable part to the movable object main body.

According to this aspect, if the movable object is configured to include the movable object main body and the movable part, the movable object main body is configured to have a movement resistance (resistance applied during movement) to the outer tube body that is larger than the movement resistance of the movable part to the movable object main body. Consequently, the minute vibrations of the first medical instrument or the second medical instrument in the axial direction can be absorbed by the slide of the movable part against the movable object main body.

An eleventh aspect is a mode of the surgical device of any one of the first to tenth aspects, wherein the insertion part of the first medical instrument further includes a part which is disposed closer to a distal end than the part having the first diameter A1, and is configured to be delivered to protrude out of the first exit port, and has a third diameter A3 smaller than the first diameter A1.

According to this aspect, the insertion part of the first medical instrument further includes the part which is disposed closer to the distal end than (on the distal end side with respect to) the part having the first diameter A1, and is delivered to protrude out of the first exit port, and has the third diameter A3. The third diameter A3 is formed smaller than the first diameter A1. Consequently, the resistance applied to the distal end part of the insertion part of the first medical instrument from the first sealing member and the first holding part during insertion of the first medical instrument into the outer tube can be reduced. The reduction can further facilitate the insertion and extraction operation of the first medical instrument.

A twelfth aspect is a mode of the surgical device of any one of the first to tenth aspects, wherein the insertion part of the first medical instrument further includes a part which is disposed closer to a distal end than the part having the first diameter A1, and is configured to be delivered to protrude out of the first exit port, and has a third diameter A3 larger than the first diameter A1.

According to this aspect, the insertion part of the first medical instrument further includes the part which is disposed closer to the distal end than (on the distal end side with respect to) the part having the first diameter A1, and is delivered to protrude out of the first exit port, and has a third diameter A3. The third diameter A3 is formed larger than the first diameter A1. Consequently, the size of the movable object contained in the outer tube can be reduced, thereby enabling the entire outer tube to have a reduced diameter.

A thirteenth aspect is a mode of the surgical device of the second aspect, wherein the insertion part of the second medical instrument further includes a part which is disposed closer to a distal end than the part having the first diameter B1, and is configured to be delivered to protrude out of the second exit port, and has a third diameter B3 smaller than the first diameter B1.

According to this aspect, the insertion part of the second medical instrument further includes the part which is disposed closer to the distal end than (on the distal end side with respect to) the part having the first diameter B1, and is delivered to protrude out of the second exit port, and has a third diameter B3. The third diameter B3 is formed smaller than the first diameter B1. Consequently, the resistance applied to the distal end part of the insertion part of the second medical instrument from the second sealing member and the second holding part during insertion of the second medical instrument into the outer tube can be reduced. The reduction can facilitate the insertion and extraction operation of the second medical instrument.

A fourteenth aspect is a mode of the surgical device of the second aspect, wherein the insertion part of the second medical instrument further includes a part which is disposed closer to a distal end than the part having the first diameter B1, and is configured to be delivered to protrude out of the second exit port, and has a third diameter B3 larger than the first diameter B1.

According to this aspect, the insertion part of the second medical instrument further includes the part which is disposed closer to the distal end than (on the distal end side with respect to) the part having the first diameter B1, is delivered to protrude out of the second exit port, and has a third diameter B3. The third diameter B3 is formed larger than the first diameter B1. Consequently, the size of the movable object contained in the outer tube can be reduced, thereby enabling the entire outer tube to have a reduced diameter.

A fifteenth aspect is an outer tube into which an insertion part of a first medical instrument and an insertion part of a second medical instrument are inserted, and is configured to guide the insertion part of the first medical instrument and the insertion part of the second medical instrument into a body cavity, the outer tube comprising: a cylindrical outer tube body into which the insertion part of the first medical instrument and the insertion part of the second medical instrument are inserted; a first entry port provided at a proximal end part of the outer tube body; a second entry port provided at the proximal end part of the outer tube body; a first sealing member which is provided at the first entry port, and configured to slidably seal the insertion part of the first medical instrument; a second sealing member which is provided at the second entry port, and configured to slidably seal the insertion part of the second medical instrument; a first exit port provided at a distal end part of the outer tube body; a second exit port provided at the distal end part of the outer tube body; a movable object which is arranged in the outer tube body and configured to be movable in the outer tube body in an axial direction; a first holding part which is provided at the movable object and configured to hold the insertion part of the first medical instrument inserted into the outer tube body; and a second holding part which is provided at the movable object and configured to hold the insertion part of the second medical instrument inserted into the outer tube body, wherein the insertion part of the first medical instrument comprises: a part which is to be held by the first holding part and has a first diameter A1; and a part which is disposed closer to a proximal end than the part having the first diameter A1, and is configured to maintain hermeticity with the first sealing member, and has a second diameter A2 larger than the first diameter A1.

According to this aspect, the outer tube is configured to include the cylindrical outer tube body, and the movable object arranged in the outer tube body. When the first medical instrument and the second medical instrument are inserted into the outer tube body, these instruments are held by the first holding part and the second holding part provided at the movable object, so as to be integrated. The movable object is configured to be movable along the axis of the outer tube body. When the first medical instrument is moved in the axial direction, the second medical instrument is moved in interlock with the movement. Likewise, when the second medical instrument is moved in the axial direction, the first medical instrument is moved in interlock with the movement. In this case, for example, if the first medical instrument is the endoscope and the second medical instrument is the treatment tool, the endoscope can be moved in interlock with the movement of the treatment tool. This movement allows the visual field (imaging region) of the endoscope to follow the treatment part, thereby allowing the operator to be always provided with an image optimal to treatment. That is, the image desired by the operator can be displayed without stress. Furthermore, the first medical instrument and the second medical instrument are inserted into the body cavity through the outer tube. Consequently, only a single site to be punctured into the body cavity wall is required. Therefore, the low-invasive operation (operation with a small load to the body) can be performed. Note that the first medical instrument visual field is moved in the forward and rear direction (to-and-fro movement) by movement of the second medical instrument in the axial direction. The movement in the vertical and horizontal directions is performed by the inclination movement of the second medical instrument. That is, all the parts including the outer tube are inclined to move the visual field. In this case, the inclination movement of the outer tube can move the visual field. Consequently, the incision is not required to be enlarged to perform treatment or move the visual field. Therefore, the low-invasive operation can be performed. Typically, laparoscopic surgery is performed in a state where gas is supplied into an abdominal cavity to expand the abdominal cavity. Because the first medical instrument entry port and the second medical instrument entry port, which are provided at the outer tube, respectively have the respective sealing members (the first sealing member and the second sealing member), the hermeticity can be secured.

Further, according to this aspect, the insertion part of the first medical instrument includes: the part which is to be held by the first holding part and has the first diameter A1; and the part which is disposed closer to the proximal end than (on the proximal end side with respect to) the part having the first diameter A1, and is configured to maintain hermeticity with the first sealing member, and has the second diameter A2 larger than the first diameter A1. Consequently, the insertion and extraction operation of the first medical instrument into and from the outer tube can be easily performed. That is, such a configuration can eliminate the sliding friction applied from the first sealing member during insertion and extraction of the first medical instrument at the distal end part side of the first medical instrument. Consequently, the insertion and extraction operation of the first medical instrument can be smoothly performed without unnecessary force. Furthermore, the load applied to the first sealing member can be reduced, and the life-span of the first sealing member can be increased. Moreover, in the first medical instrument, the part exposed from the proximal end part of the outer tube is formed thick. Consequently, the instrument becomes resistant to deformation, and direct operational feeling with high stiffness can be obtained. Furthermore, because the diameter of the first holding part can be reduced, the size of the movable object contained in the outer tube can also be reduced, which can, in turn, reduce the entire size of the outer tube.

Note that it is preferable that the part where the diameter is varied be formed so as to allow the diameter to be smoothly varied.

A sixteenth aspect is a mode of the outer tube of the fifteenth aspect, wherein the insertion part of the second medical instrument includes: a part which is to be held by the second holding part and has a first diameter B1; and a part which is disposed closer to a proximal end than (on a proximal end side with respect to) the part having the first diameter B1 and has a second diameter B2 for maintaining hermeticity with the second sealing member, the second diameter B2 being larger than the first diameter B1.

According to this aspect, the second medical instrument is also formed as with the first medical instrument. Consequently, also for the second medical instrument, advantageous working-effects analogous to the effects of the first medical instrument can be achieved.

It is preferable that the second medical instrument be formed such that the part where the diameter is varied be formed so as to allow the diameter to be smoothly varied.

A seventeenth aspect is a mode of the outer tube of the fifteenth or sixteenth aspect, wherein the first medical instrument is an endoscope.

According to this aspect, the first medical instrument is configured by the endoscope. Consequently, the endoscope can be moved in interlock with the movement of the second medical instrument (e.g., treatment tool), and the image desired by the operator can be displayed without stress.

An eighteenth aspect is a mode of the outer tube of the seventeenth aspect, wherein the endoscope is an endoscope that internally includes an imaging device (imaging means) at a distal end of the insertion part.

According to the outer tube of this aspect, the imaging means is internally included at the distal end of the insertion part of the endoscope.

A nineteenth aspect is a mode of the outer tube of the fifteenth or sixteenth aspect, wherein the first medical instrument is a treatment tool.

According to this aspect, the first medical instrument is configured by the treatment tool. Consequently, the second medical instrument (e.g., endoscope) can be moved in interlock with the movement of the treatment tool.

A twentieth aspect is a mode of the outer tube of any one of the fifteenth to nineteenth aspects, wherein the first holding part can adjust a holding position of the insertion part of the first medical instrument.

According to this aspect, the position of the insertion part of the first medical instrument held by the first holding part can be adjusted in the axial direction. Consequently, the relative positional relationship (the positional relationship of the distal end) between the first medical instrument and the second medical instrument that are connected via the movable object can be adjusted. Accordingly, for example, if the first medical instrument or the second medical instrument is configured by an endoscope, the imaging range can be adjusted and the usability can be improved.

A twenty-first aspect is a mode of the outer tube of any one of the fifteenth to twentieth aspects, wherein the second holding part can adjust a holding position of the insertion part of the second medical instrument.

According to this aspect, the position of the insertion part of the second medical instrument held by the second holding part can be adjusted in the axial direction. Consequently, the relative positional relationship (the positional relationship of the distal end) between the first medical instrument and the second medical instrument that are connected via the movable object can be adjusted. Accordingly, for example, if the first medical instrument or the second medical instrument is configured by an endoscope, the imaging range can be adjusted and the usability can be improved.

A twenty-second aspect is a mode of the outer tube of any one of the fifteen to twenty-first aspects, wherein the first sealing member has a hole and is configured by a plate-shaped elastic body, the first holding part includes an annular elastic member through which the insertion part of the first medical instrument is inserted, and the hole of the first sealing member is configured to have a diameter that is larger than an inner diameter of the elastic member of the first holding part.

According to this aspect, the first sealing member is configured by the plate-shaped elastic body, and is provided with the hole into which the first medical instrument is inserted. If the insertion part of the first medical instrument is inserted into the hole, the gap formed between the first entry port is sealed. According to this aspect, the first holding part includes the annular elastic member, and the insertion part of the first medical instrument is inserted into the annular elastic member, thereby enabling the first medical instrument to be held. Consequently, the position of the insertion part of the first medical instrument held by the first holding part can be adjusted in the axial direction. According to this aspect, in the outer tube, the diameter of the hole which is provided at the first sealing member is configured to be larger than the inner diameter of the elastic member of the first holding part. Consequently, the insertion and extraction operation of the first medical instrument for the outer tube can be easily performed.

A twenty-third aspect is a mode of the outer tube of any one of the fifteenth to twenty-second aspects, wherein the movable object includes: a movable object main body configured to be movable with respect to the outer tube body in the axial direction; and a movable part configured to be movable with respect to the movable object main body in the axial direction, and one of the first holding part and the second holding part is provided in the movable part, and another one of the first holding part and the second holding part is provided in the movable object main body.

According to this aspect, the movable object is configured to include the movable object main body configured to be movable in the axial direction with respect to the outer tube body, and the movable part configured to be movable in the axial direction with respect to the movable object main body. And, one of the first holding part and the second holding part is provided in the movable part, and another one of these parts is provided in the movable object main body. Consequently, interlocked movement of the first medical instrument and the second medical instrument can have "play (non-sensitive region)". That is, within a predetermined range (movable range), the movement of the first medical instrument can be prevented from being transmitted to the second medical instrument (the movement of the second medical instrument can be prevented from being transmitted to the first medical instrument). Such interlocked movement of the first medical instrument and the second medical instrument is thus provided with "play". Consequently, for example, in the case where the first medical instrument is configured by an endoscope, minute movement of the second medical instrument in the axial direction (to-and-fro movement with a small amplitude and the like) can be prevented from being transmitted to the endoscope. Therefore, the image on the screen can be prevented from swaying due to minute movement of the second medical instrument. An easily viewable image can be always provided for the operator.

A twenty-fourth aspect is a mode of the outer tube of the twenty-third aspect, wherein the movable object main body is configured to have a greater movement resistance to the outer tube body than a movement resistance of the movable part to the movable object main body.

According to this aspect, if the movable object is configured to include the movable object main body and the movable part, the movable object main body is configured to have a movement resistance (resistance applied during movement) to the outer tube body that is larger than the movement resistance of the movable part to the movable object main body. Consequently, the minute vibrations of the first medical instrument or the second medical instrument in the axial direction can be absorbed by the slide of the movable part against the movable object main body.

A twenty-fifth aspect is a mode of the outer tube of any one of the fifteenth to twenty-fourth aspects, wherein the insertion part of the first medical instrument further includes a part which is disposed closer to a distal end than the part having the first diameter A1, and is configured to be delivered to protrude out of the first exit port, and has a third diameter A3 smaller than the first diameter A1.

According to this aspect, the insertion part of the first medical instrument further includes the part which is disposed closer to the distal end than (on the distal end side with respect to) the part having the first diameter A1, and is delivered to protrude out of the first exit port, and has a third diameter A3. The third diameter A3 is formed smaller than the first diameter A1. Consequently, the resistance applied to the distal end part of the insertion part of the first medical instrument from the first sealing member and the first holding part during insertion of the first medical instrument into the outer tube can be reduced. The reduction can further facilitate the insertion and extraction operation of the first medical instrument.

A twenty-sixth aspect is a mode of the outer tube of any one of the fifteenth to twenty-fourth aspects, wherein the insertion part of the first medical instrument further includes a part which is disposed closer to a distal end than the part having the first diameter A1, and is configured to be delivered to protrude out of the first exit port, and has a third diameter A3 larger than the first diameter A1.

According to this aspect, the insertion part of the first medical instrument further includes the part which is disposed closer to the distal end than (on the distal end side with respect to) the part having the first diameter A1, and is delivered to protrude out of the first exit port, and has a third diameter A3. The third diameter A3 is formed larger than the first diameter A1. Consequently, the size of the movable object contained in the outer tube can be reduced, thereby enabling the entire outer tube to be narrowed.

A twenty-seventh aspect is a mode of the outer tube of the sixteenth aspect, wherein the insertion part of the second medical instrument further includes a part which is disposed closer to a distal end than the part having the first diameter B1, and is configured to be delivered to protrude out of the second exit port, and has a third diameter B3 smaller than the first diameter B1.

According to this aspect, the insertion part of the second medical instrument further includes the part which is disposed closer to the distal end than (on the distal end side with respect to) the part having the first diameter B1, and is delivered to protrude out of the second exit port, and has a third diameter B3. The third diameter B3 is formed smaller than the first diameter B1. Consequently, the resistance applied to the distal end part of the insertion part of the second medical instrument from the second sealing member and the second holding part during insertion of the second medical instrument into the outer tube can be reduced. The reduction can facilitate the insertion and extraction operation of the second medical instrument.

A twenty-eighth aspect is a mode of the outer tube of the sixteenth aspect, wherein the insertion part of the second medical instrument further includes a part which is disposed closer to a distal end than the part having the first diameter B1, and is configured to be delivered to protrude out of the second exit port, and has a third diameter B3 larger than the first diameter B1.

According to this aspect, the insertion part of the second medical instrument further includes the part which is disposed closer to the distal end than (on the distal end side with respect to) the part having the first diameter B1, is delivered to protrude out of the second exit port, and has a third diameter B3. The third diameter B3 is formed larger than the first diameter B1. Consequently, the size of the movable object contained in the outer tube can be reduced, thereby enabling the entire outer tube to be narrowed.

A twenty-ninth aspect is an endoscope to be inserted into a body cavity through an outer tube which comprises: a cylindrical outer tube body into which an insertion part of the endoscope and an insertion part of a treatment tool are inserted; an endoscope entry port provided at a proximal end part of the outer tube body; a treatment tool entry port provided at the proximal end part of the outer tube body; an endoscope sealing member which is provided at the endoscope entry port and configured to slidably seal the insertion part of the endoscope; a treatment tool sealing member which is provided at the treatment tool entry port and configured to slidably seal the insertion part of the treatment tool; an endoscope exit port provided at a distal end part of the outer tube body; a treatment tool exit port provided at the distal end part of the outer tube body; a movable object which is arranged in the outer tube body and configured to be movable in the outer tube body in an axial direction; an endoscope holding part which is provided at the movable object and configured to hold the insertion part of the endoscope inserted into the outer tube body; and a treatment tool holding part which is provided at the movable object and configured to hold the insertion part of the treatment tool inserted into the outer tube body, in which the insertion part comprises: a part which is to be held by the endoscope holding part and has a first diameter A1; and a part which is disposed closer to a proximal end than the part having the first diameter A1, and is configured to maintain hermeticity with the endoscope sealing member, and has a second diameter A2 larger than the first diameter A1.

According to this aspect, the insertion part of the endoscope includes: the part which is to be held by the endoscope holding part and has the first diameter A1; and the part which is disposed closer to the proximal end than (on the proximal end side with respect to), and is configured to maintain hermeticity with the endoscope sealing member, and has the second diameter A2. The second diameter A2 is formed larger than the first diameter A1. Consequently, the insertion and extraction operation of the endoscope into and from the outer tube can be easily performed. That is, such a configuration can eliminate the sliding friction applied from the endoscope sealing member during insertion and extraction of the endoscope at the distal end part side of the endoscope. Consequently, the insertion and extraction operation of the endoscope can be smoothly performed without unnecessary force. Furthermore, the load applied to the endoscope sealing member can be reduced, and the life-span of the endoscope sealing member can be increased. Moreover, in the endoscope according to this aspect, the part exposed from the proximal end part of the outer tube is formed thick. Consequently, the endoscope becomes resistant to deformation, and direct operational feeling with high stiffness can be obtained. Furthermore, because the diameter of the endoscope holding part can be reduced, the size of the movable object contained in the outer tube can also be reduced, which can, in turn, reduce the entire size of the outer tube.

Note that it is preferable that the part where the diameter is varied be formed so as to allow the diameter to be smoothly varied.

A thirtieth aspect is a mode of the endoscope of the twenty-ninth aspect, wherein the insertion part further includes a part which is disposed closer to a distal end than the part having the first diameter A1, and is configured to be delivered to protrude out of the endoscope exit port, and has a third diameter A3 smaller than the first diameter A1.

According to this aspect, the insertion part of the endoscope further includes the part which is disposed closer to the distal end than (on the distal end side with respect to) the part having the first diameter A1, and is delivered to protrude out of the endoscope exit port, and has a third diameter A3. The third diameter A3 is formed smaller than the first diameter A1. Consequently, it is possible to reduce the resistance applied to the distal end part of the insertion part of the endoscope from the endoscope sealing member and the endoscope holding part during insertion of the endoscope into the outer tube. The reduction can further facilitate the insertion and extraction operation of the endoscope.

A thirty-first aspect is a mode of the endoscope of the twenty-ninth aspect, wherein the insertion part further includes a part which is disposed closer to a distal end than the part having the first diameter A1, and is configured to be delivered to protrude out of the endoscope exit port, and has a third diameter A3 larger than the first diameter A1.

According to this aspect, the insertion part of the endoscope further includes the part which is disposed closer to the distal end than (on the distal end side with respect to) the part having the first diameter A1, and is delivered to protrude out of the endoscope exit port, and has a third diameter A3. The third diameter A3 is formed larger than the first diameter A1. Consequently, the size of the movable object contained in the outer tube can be reduced, thereby enabling the entire outer tube to have a reduced diameter.

A thirty-second aspect is a mode of the endoscope of any one of the twenty-ninth to thirty-first aspects, wherein imaging means is internally included at a distal end of the insertion part.

According to the surgical device of this aspect, the imaging means is internally included at the distal end of the insertion part of the endoscope.

A thirty-third aspect is a treatment tool to be inserted into a body cavity through an outer tube which comprises: a cylindrical outer tube body into which an insertion part of the endoscope and an insertion part of a treatment tool are inserted; an endoscope entry port provided at a proximal end part of the outer tube body; a treatment tool entry port provided at the proximal end part of the outer tube body; an endoscope sealing member which is provided at the endoscope entry port and configured to slidably seal the insertion part of the endoscope; a treatment tool sealing member which is provided at the treatment tool entry port and configured to slidably seal the insertion part of the treatment tool; an endoscope exit port provided at a distal end part of the outer tube body; a treatment tool exit port provided at the distal end part of the outer tube body; a movable object which is arranged in the outer tube body and configured to be movable in the outer tube body in an axial direction; an endoscope holding part which is provided at the movable object and configured to hold the insertion part of the endoscope inserted into the outer tube body; and a treatment tool holding part which is provided at the movable object and configured to hold the insertion part of the treatment tool inserted into the outer tube body, in which the insertion part includes: a part which is to be held by the treatment tool holding part and has a first diameter B1; and a part which is disposed closer to a proximal end than the part having the first diameter B1, and is configured to maintain hermeticity with the treatment tool sealing member, and has a second diameter B2 larger than the first diameter B1.

According to this aspect, the insertion part of the treatment tool includes: the part which is to be held by the treatment tool holding part and has the first diameter B1; and the part which is disposed closer to the proximal end than (on the proximal end side with respect to) the part having the first diameter B1, and configured to maintain hermeticity with the treatment tool sealing member, and has the second diameter B2. The second diameter B2 is formed larger than the first diameter B1. Consequently, the insertion and extraction operation of the treatment tool into and from the outer tube can be easily performed. That is, such a configuration can eliminate the sliding friction applied from the treatment tool sealing member during insertion and extraction of the treatment tool at the distal end part side of the treatment tool. Consequently, the insertion and extraction operation of the treatment tool can be performed without unnecessary force. Furthermore, the load applied to the treatment tool sealing member can be reduced, and the life-span of the treatment tool sealing member can be increased. Moreover, in the treatment tool, the part exposed from the proximal end part of the outer tube is formed thick. Consequently, the tool becomes resistant to deformation, and direct operational feeling with high stiffness can be obtained. Furthermore, because the diameter of the treatment tool holding part can be reduced, the size of the movable object contained in the outer tube can also be reduced, which can, in turn, reduce the entire size of the outer tube.

Note that it is preferable that the part where the diameter is varied be formed so as to allow the diameter to be smoothly varied.

A thirty-fourth aspect is a mode of the treatment tool of the thirty-third aspect, wherein the insertion part further includes a part which is disposed closer to a distal end than the part having the first diameter B1, and is configured to be delivered to protrude out of the treatment tool exit port, and has a third diameter B3 smaller than the first diameter B1.

According to this aspect, the insertion part of the treatment tool further includes the part which is disposed closer to the distal end than (on the distal end side with respect to) the part having the first diameter B1, and is delivered to protrude out of the treatment tool exit port, and has a third diameter B3. The third diameter B3 is formed smaller than the first diameter B1. Consequently, the resistance applied to the distal end part of the insertion part of the treatment tool from the treatment tool sealing member and the treatment tool holding part during insertion of the treatment tool into the outer tube can be reduced. The reduction can further facilitate the insertion and extraction operation of the treatment tool.

A thirty-fifth aspect is a mode of the treatment tool of the thirty-third aspect, wherein the insertion part further includes a part which is disposed closer to a distal end than the part having the first diameter B1, and is configured to be delivered to protrude out of the treatment tool exit port, and has a third diameter B3 larger than the first diameter B1.

According to this aspect, the insertion part of the treatment tool further includes the part which is disposed closer to the distal end than (on the distal end side with respect to) the part having the first diameter B1, and is delivered to protrude out of the treatment tool exit port, and has a third diameter B3. The third diameter B3 is formed larger than the first diameter B1. Consequently, the size of the movable object contained in the outer tube can be reduced, thereby enabling the entire outer tube to be narrowed.

The present invention can allow two medical instruments to be moved in interlocked with each other using a simple configuration, and can provide a surgical device, an outer tube, an endoscope, and a treatment tool that achieve excellent operability. Furthermore, the present invention can provide the surgical device, the outer tube, the endoscope, and the treatment tool that have excellent insertion and extraction operability into and from the outer tube.

DETAILED DESCRIPTION OF THE EMBODIMENTS

Hereinafter, preferred embodiments of the present invention are described with reference to the accompanying drawings.

<<Configuration of Endoscopic Surgical Device>>

Figure 1:
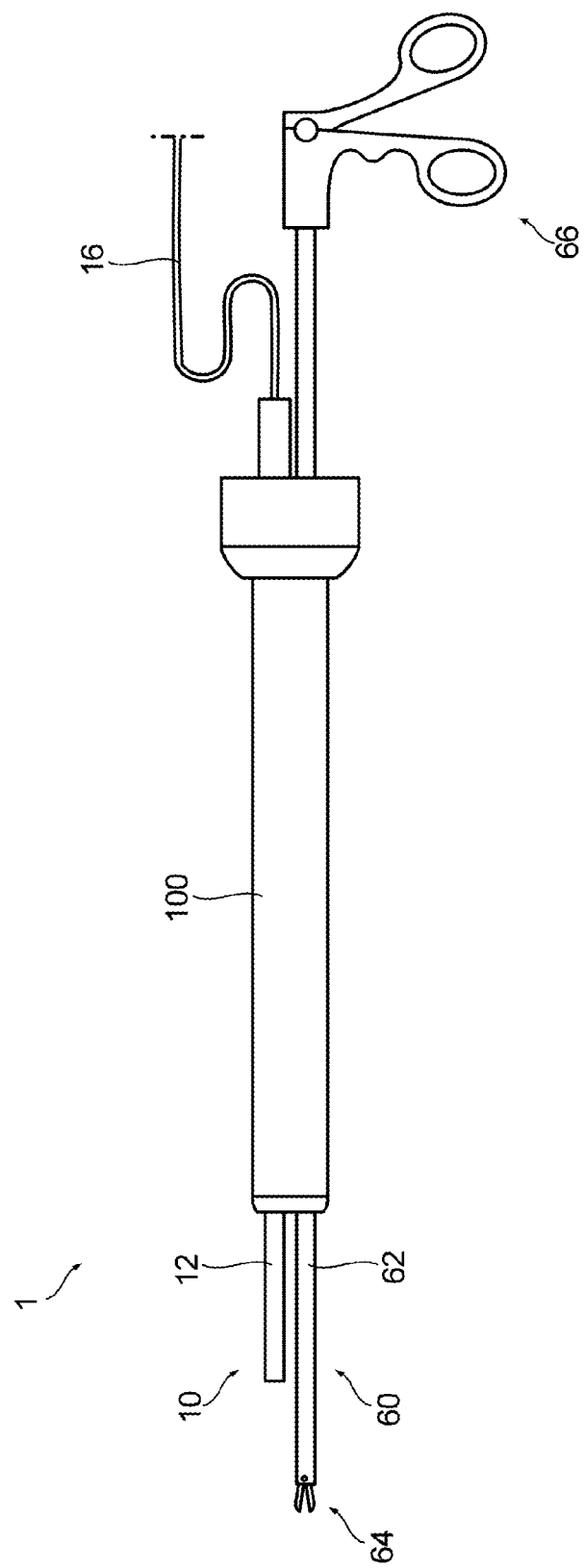
FIG. 1 is a schematic configuration diagram of an endoscopic surgical device.

FIG. 1 is a schematic configuration diagram of an endoscopic surgical device.

The endoscopic surgical device 1 as a surgical device is configured to include: an endoscope 10 that is to be inserted into a body cavity of a patient and is for observing the inside of the body cavity; a treatment tool 60 that is to be inserted into the body cavity of the patient and is for performing necessary treatment; and an outer tube 100 for guiding the endoscope 10 and the treatment tool 60 into the body cavity of the patient.

<Endoscope>

Figure 2:
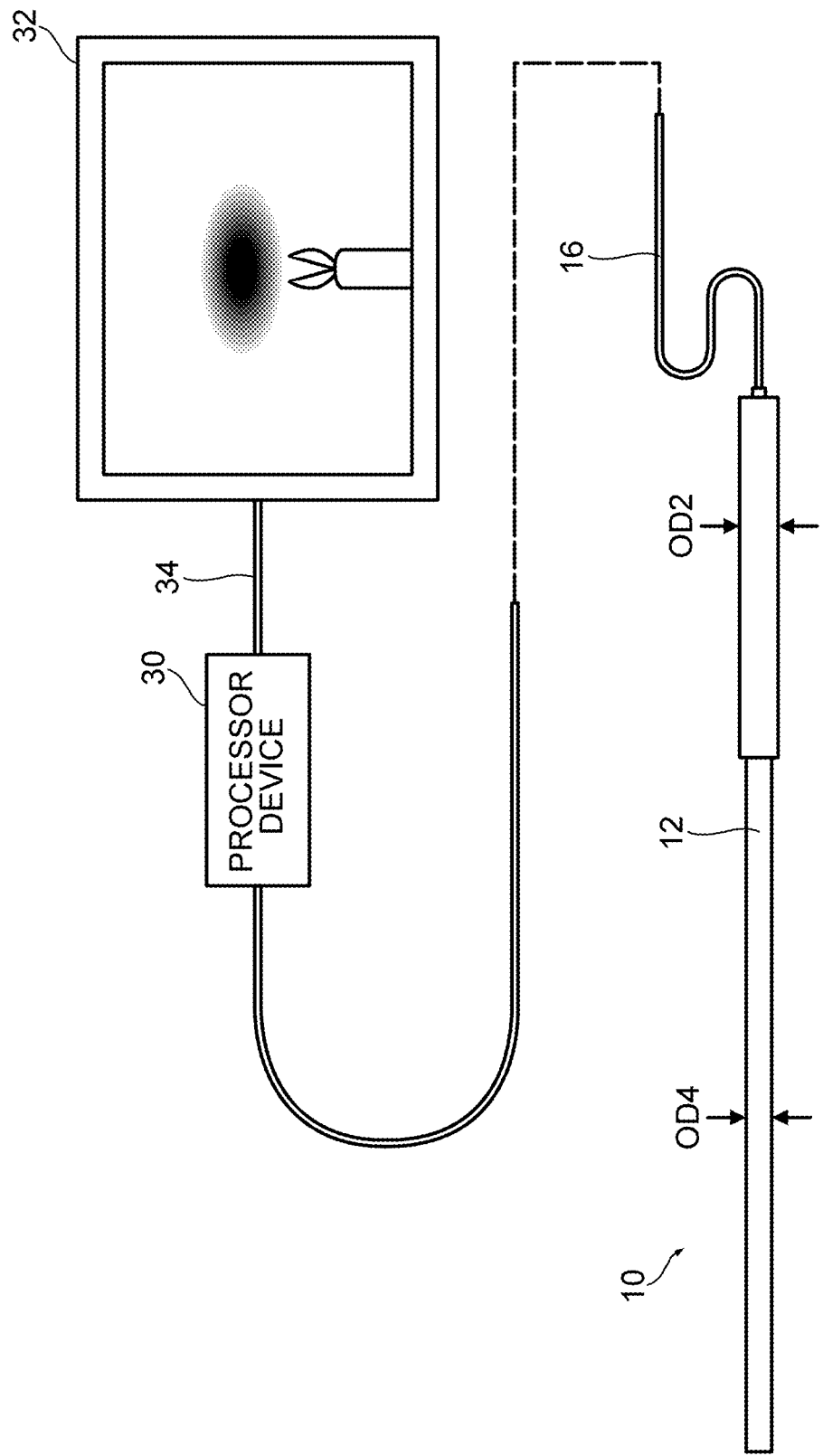
FIG. 2 is a schematic configuration diagram of an endoscope system.

FIG. 2 is a schematic configuration diagram of an endoscope system.

The endoscope 10 as a medical instrument is an electronic endoscope, and configures the endoscope system together with a processor device 30, and a monitor 32.

The endoscope 10 used in the endoscopic surgical device 1 of this embodiment is a rigid endoscope, such as a laparoscope. The endoscope 10 includes a linear-rod-shaped insertion part 12.

The insertion part 12 includes an observation window 14 (see FIG. 3) at its distal end. The endoscope 10 allows observation in the body cavity through the observation window 14 at a distal end of the insertion part 12.

Figure 3:
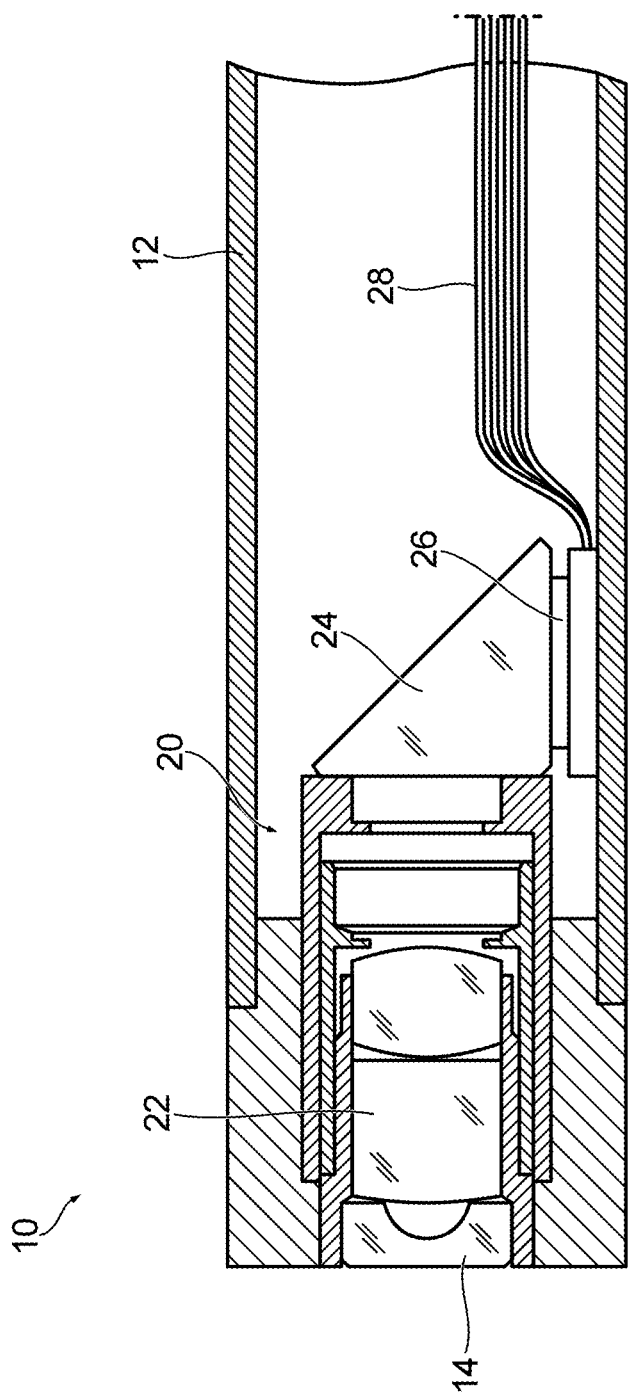
FIG. 3 is a sectional view showing a schematic configuration of the inside of a distal end part of an insertion part of an endoscope.

FIG. 3 is a sectional view showing a schematic configuration of the inside of a distal end part of the insertion part of the endoscope.

As shown in FIG. 3, the insertion part 12 internally includes an imaging device 20, which is imaging means, at the distal end part. An image observed through the observation window 14 is taken by the imaging device 20.

The imaging device 20 is configured to include a lens group 22, a prism 24, an image pickup element 26 (CCD (Charge Coupled Device), a CMOS (Complementary Metal Oxide Semiconductor), etc.) and the like.

Subject light entering from the observation window 14 passes through the lens group 22, is subsequently reflected by the prism 24 at a substantially right angle, and is incident on the light receiving surface of the image pickup element 26. Consequently, an image observed through the observation window 14 is taken by the image pickup element 26.

Various signal lines 28 connected to the imaging device 20 are arranged inside the insertion part 12, and extracted from a proximal end part of the insertion part 12 through a cable 16 for the endoscope.

The processor device 30 is a device that integrally controls the entire endoscope system. The processor device 30 is connected to the endoscope 10 through the cable 16 for the endoscope extending from the proximal end of the insertion part 12. This device is also connected to the monitor 32 through a cable 34 for the monitor.

Electric power and control signals for operating the imaging device 20 are transmitted from the processor device 30 to the endoscope 10. On the other hand, an image signal output from the imaging device 20 is transmitted from the endoscope 10 to the processor device 30.

The processor device 30 processes the image signal obtained from the endoscope 10, and outputs the processed signal to the monitor 32. Consequently, the image of the inside of the body cavity observed through the observation window 14 of the endoscope 10 is displayed on the monitor 32.

Note that the endoscope 10 of this example includes no illumination means. Illumination is provided through another piece of means, for example a needle light. Omission of the illumination means that is to be embedded in the endoscope allows the diameter of the insertion part of the endoscope to be narrowed. Consequently, the diameter of the outer tube 100 can also be narrowed, and the invasiveness applied to a body wall of the patient can be reduced.

The endoscope 10 of this example has the configuration including the imaging device 20 at the distal end part of the insertion part 12. Alternatively, a configuration that includes the imaging device 20 at the proximal end part of the insertion part 12 may be adopted. That is, a configuration where an image observed through the observation window 14 is transmitted by a relay lens and the like and taken by the imaging device provided at the proximal end part of the insertion part 12 may be adopted.

The endoscope 10 requires use of the outer tube 100 as a precondition. Consequently, the external shape of the endoscope is made suitable for the structure of the outer tube 100. This point will be described later in detail.

<Needle Light>

Figure 4:
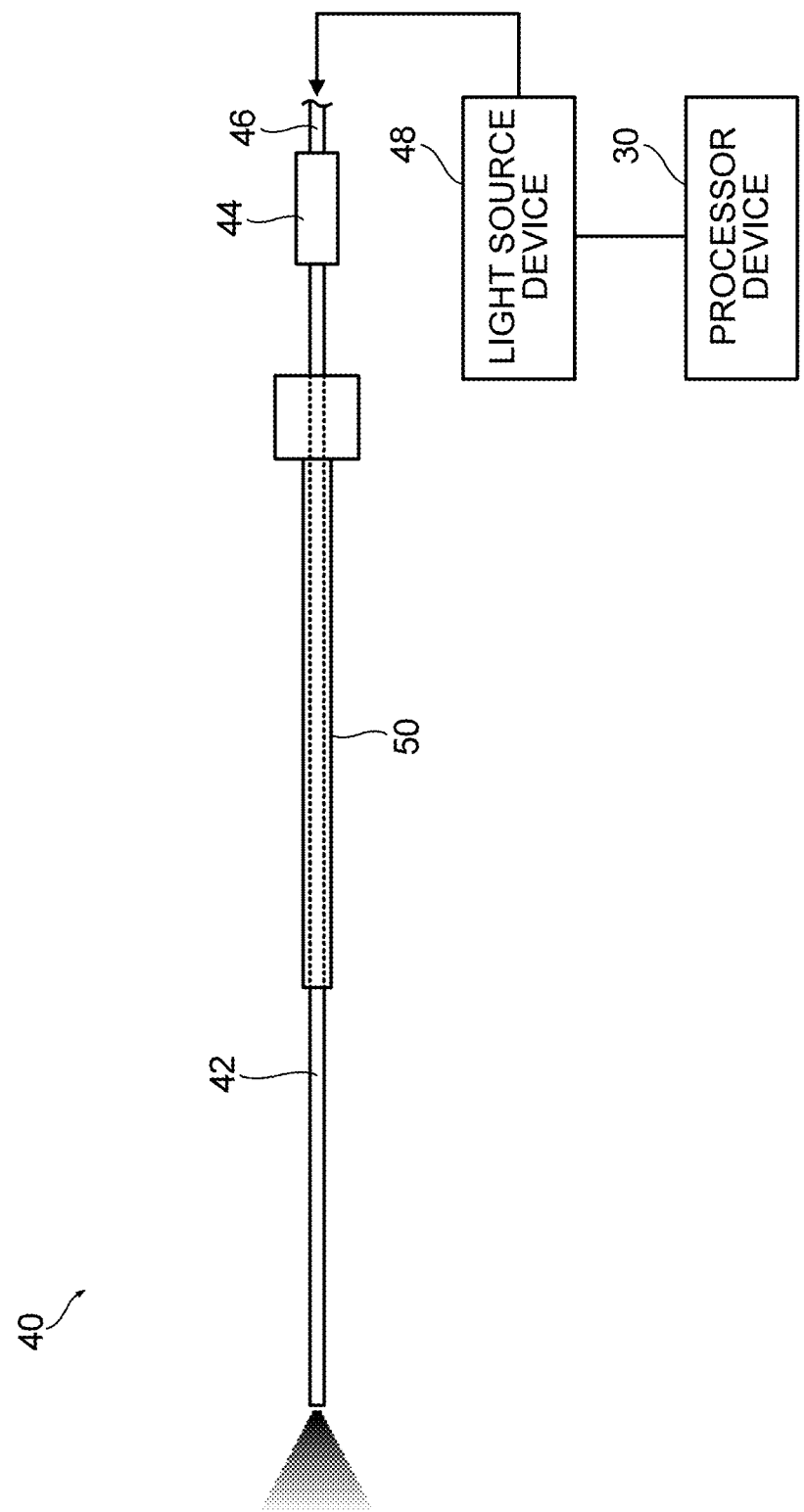
FIG. 4 is a schematic configuration diagram showing an example of a needle light.

FIG. 4 is a schematic configuration diagram showing an example of a needle light.

The needle light 40 as a medical instrument is inserted into the body cavity of the patient and illuminates the body cavity with illumination light.

The needle light 40 includes a linear-rod-shaped insertion part 42. An illumination window (not shown) is provided at the distal end of the insertion part 42. Through the illumination window, the illumination light is emitted in the axial direction. An optical fiber bundle that transmits illumination light emitted from the illumination window is contained inside the insertion part 42.

A connection part 44 is provided at the proximal end of the needle light 40. A flexible cable 46 for the needle light is connected to the connection part 44. A light source device 48 is connected through this cable 46 for the needle light. The illumination light caused to be emitted through the illumination window is supplied from the light source device 48. The light source device 48 is connected to the processor device 30 through a cable. The light intensity and the like are thus controlled.

As an example, the needle light 40 is inserted into the body cavity through an outer tube 50 for the needle light.

<Treatment Tool>

Figure 5:
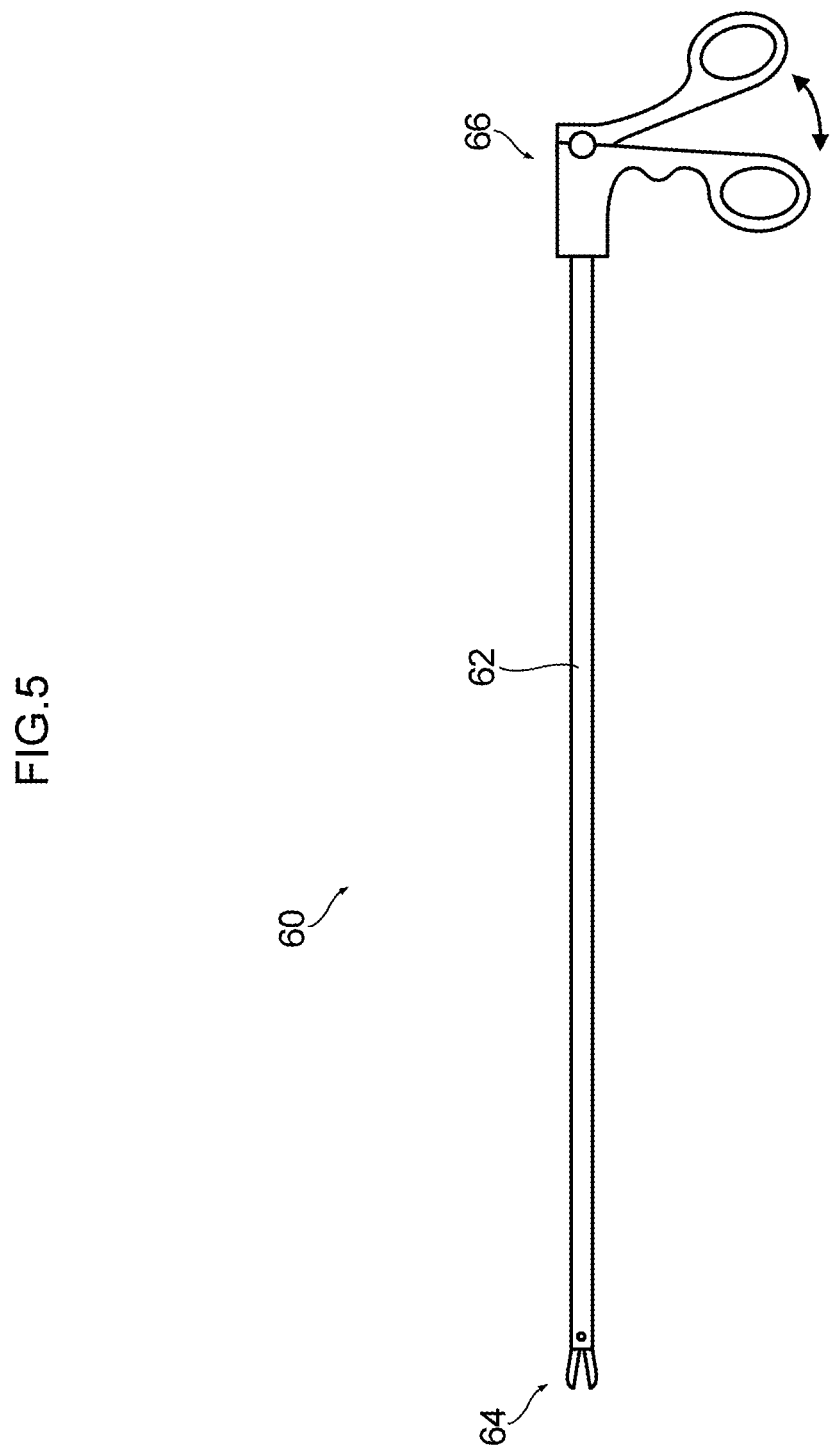
FIG. 5 is a schematic configuration diagram showing an example of a treatment tool.

FIG. 5 is a schematic configuration diagram showing an example of the treatment tool.

The treatment tool 60 as a medical instrument includes: a linear-rod-shaped insertion part 62 that is inserted into the body cavity; a treatment part 64 that is arranged at the proximal end of the insertion part 62; and a handle part (operation part) 66 that is arranged at the distal end of the insertion part 62. The treatment part 64 shown in FIG. 5 has a structure of scissors. The treatment part 64 is operated to open and close by an open and close operation of the handle part 66.

Note that the treatment tool 60 is not limited to this example. Alternatively, forceps, a laser probe, a suture instrument, an electric scalpel, a needle holder, an ultrasonic aspirator or the like may be used as the treatment tool.

<Outer Tube>

The body cavity wall of the patient is punctured with the outer tube 100. The endoscope 10 and the treatment tool 60 are inserted along the inner circumference part of the outer tube, which allows the endoscope 10 and the treatment tool 60 to be guided into the body cavity of the patient.

Figure 6:
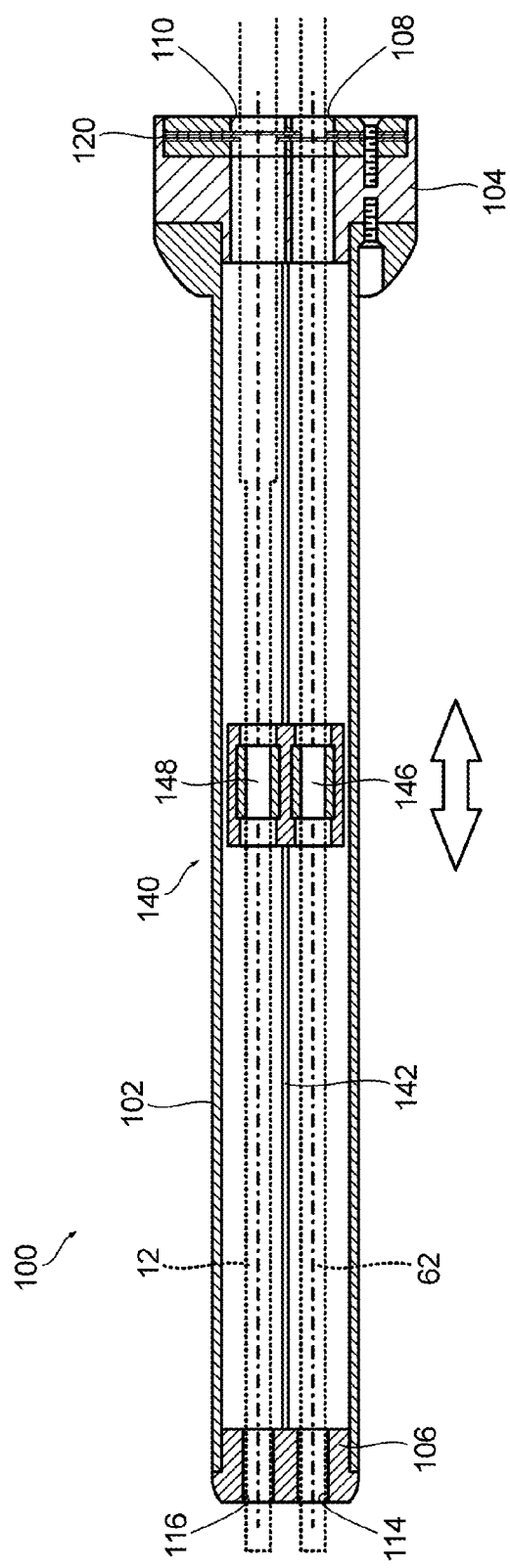
FIG. 6 is a side sectional view of an outer tube.
Figure 7:
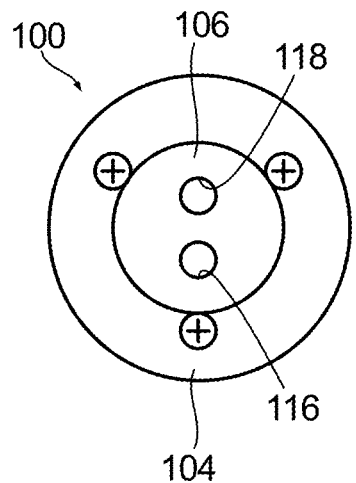
FIG. 7 is a front view of the outer tube.
Figure 8:
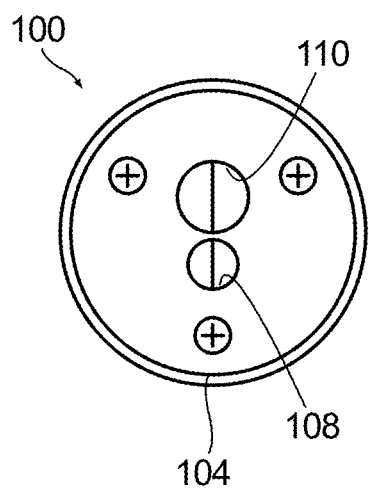
FIG. 8 is a rear view of the outer tube.
Figure 9:
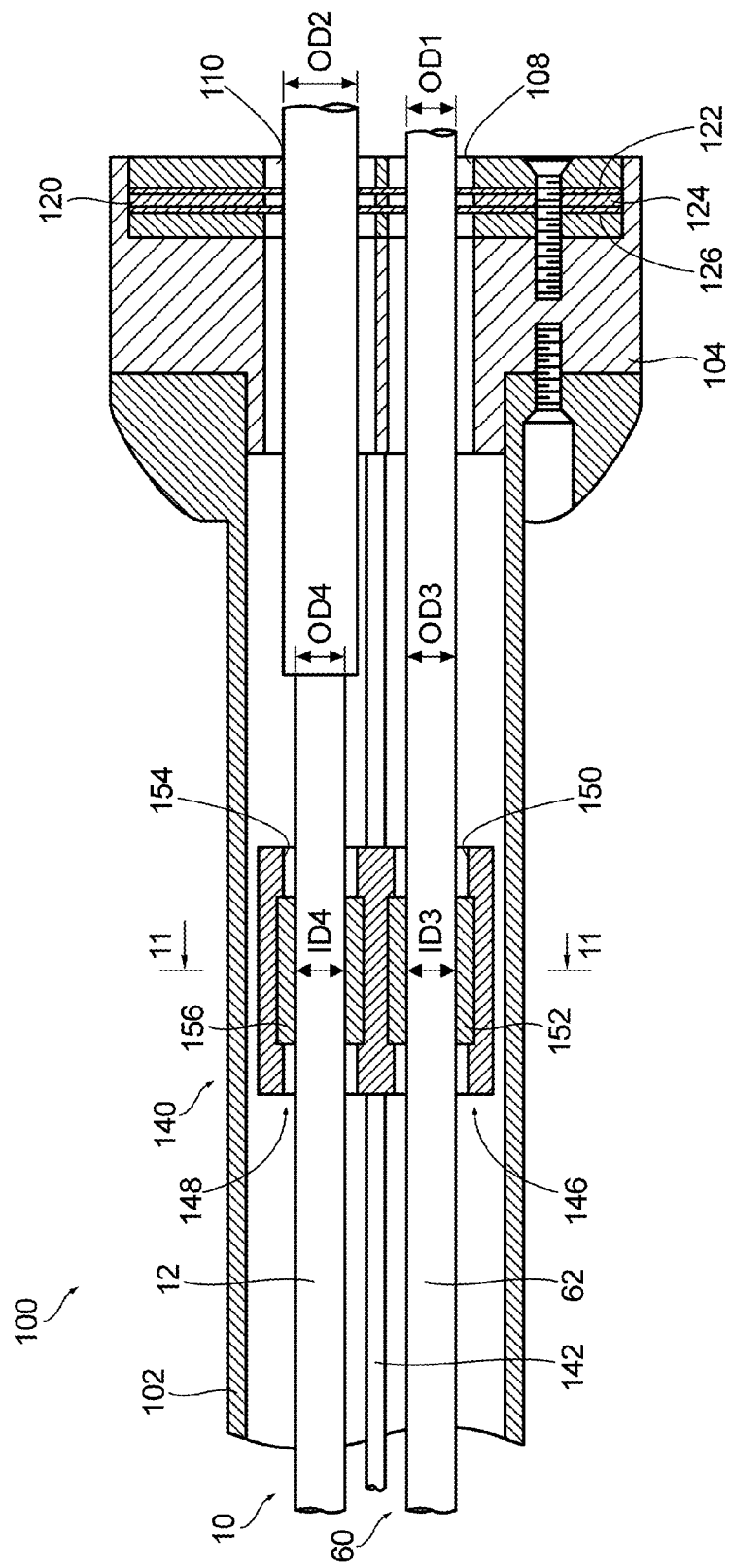
FIG. 9 is an enlarged sectional view of a proximal end part of the outer tube.
Figure 10:
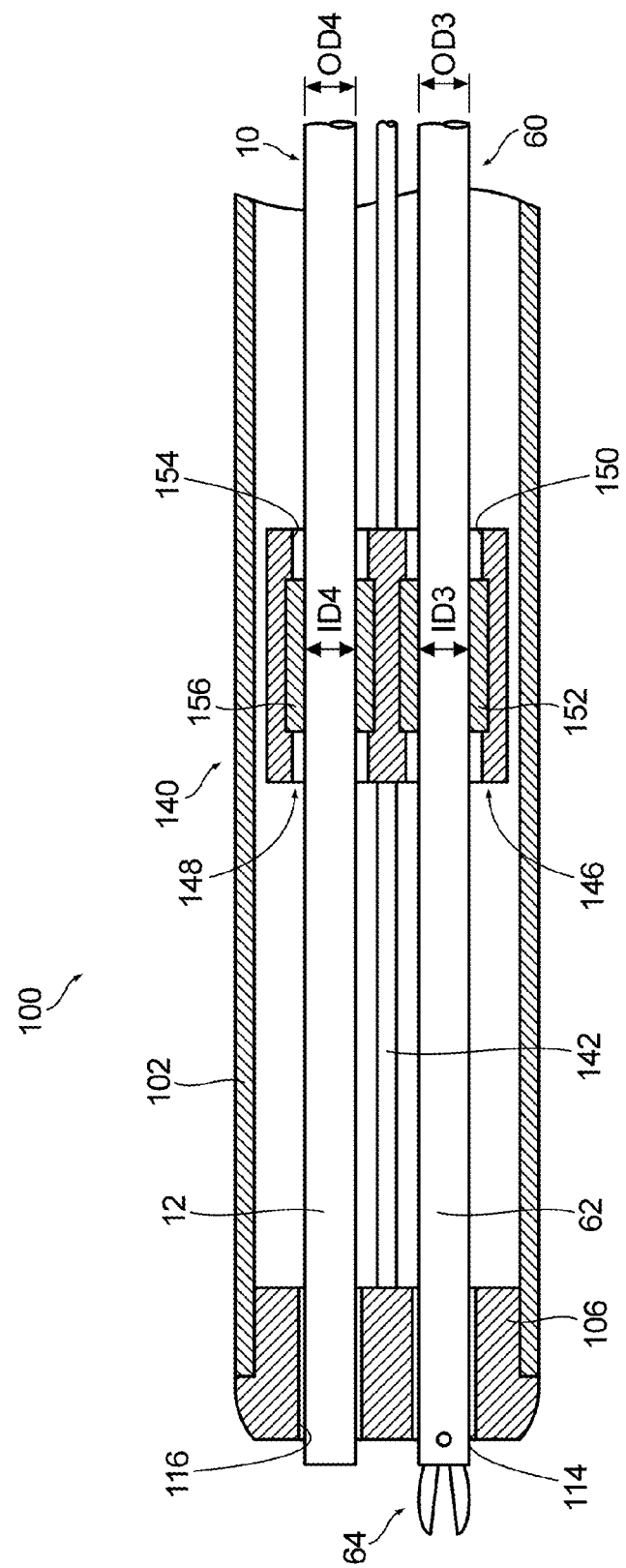
FIG. 10 is an enlarged sectional view of a distal end part of the outer tube.
Figure 11:
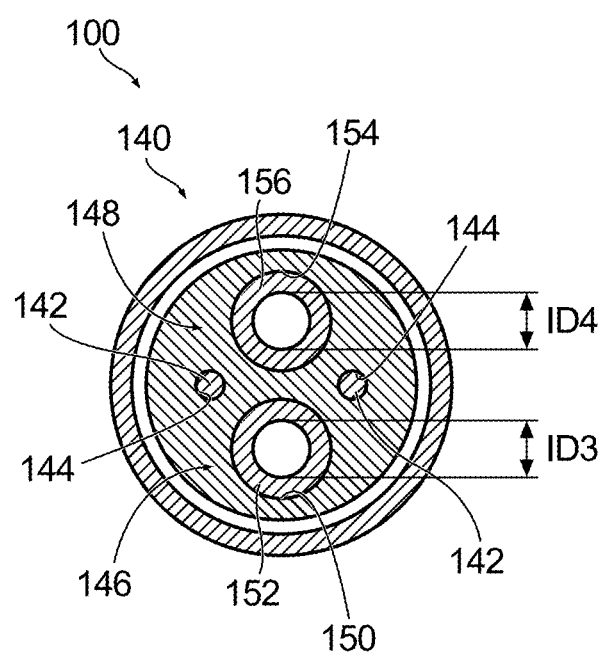
FIG. 11 is a sectional view taken along 11-11 of FIG. 9.

FIG. 6 is a side sectional view of the outer tube. FIG. 7 is a front view of the outer tube. FIG. 8 is a rear view of the outer tube. FIG. 9 is an enlarged sectional view of a proximal end part of the outer tube. FIG. 10 is an enlarged sectional view of a distal end part of the outer tube. FIG. 11 is a sectional view taken along 11-11 of FIG. 9.

The outer tube 100 includes a cylindrical outer tube body 102. The outer tube body 102 has a cylindrical shape, and the proximal end part is formed to have a flange shape with an enlarged diameter.

A proximal end cap 104 is attached to the proximal end part of the outer tube body 102. An opening part of the outer tube body 102 at the proximal end is blocked with the proximal end cap 104. A distal end cap 106 is attached to the distal end part of the outer tube body 102. An opening part of the outer tube body 102 at the distal end is blocked with the distal end cap 106.

As shown in FIG. 8, the proximal end cap 104 is provided with an endoscope entry port 110 as a first entry port for allowing the insertion part 12 of the endoscope 10 to be inserted into the outer tube body 102, and a treatment tool entry port 108 as a second entry port for allowing the insertion part 62 of the treatment tool 60 to be inserted into the outer tube body 102.

The treatment tool entry port 108 has a circular shape, and is formed to have a size allowing the insertion part 62 of the treatment tool 60 to be inserted through the port. That is, the port is formed to have a size which makes the thickest portion of the insertion part 62 of the treatment tool 60 to be inserted into the outer tube 100 insertable into the port.

The endoscope entry port 110 has a circular shape, and is formed to have a size allowing the insertion part 12 of the endoscope 10 to be inserted through the port. That is, the port is formed to have a size which makes the thickest portion of the insertion part 12 of the endoscope 10 to be inserted into the outer tube 100 insertable into the port.

As shown in FIG. 6, the distal end cap 106 is provided with an endoscope exit port 116 as a first exit port from which the insertion part 12 of the endoscope 10 inserted from the endoscope entry port 110 into the outer tube body 102 is delivered to protrude, and a treatment tool exit port 114 as a second exit port from which the insertion part 62 of the treatment tool 60 inserted into the outer tube body 102 is delivered to protrude.

The treatment tool exit port 114 has a circular shape, and is formed to have a size allowing the distal end part of the insertion part 62 of the treatment tool 60 to be inserted into the port. Preferably, the treatment tool exit port 114 has a diameter substantially identical to the outer diameter of the distal end part of the insertion part 62 of the treatment tool 60.

The endoscope exit port 116 has a circular shape, and is formed to have a size allowing the distal end part of the insertion part 12 of the endoscope 10 to be inserted into the port. Preferably, the endoscope exit port 116 has a diameter substantially identical to the outer diameter of the distal end part of the insertion part 12 of the endoscope 10.

The treatment tool entry port 108 and the treatment tool exit port 114 are coaxially arranged, and arranged on an axis parallel to the axis of the outer tube body 102. Consequently, the treatment tool 60 inserted through the treatment tool entry port 108 is delivered along the axis of the outer tube body 102 and protrudes out of the treatment tool exit port 114.

The endoscope entry port 110 and the endoscope exit port 116 are coaxially arranged, and arranged on an axis parallel to the axis of the outer tube body 102. Consequently, the endoscope 10 inserted through the endoscope entry port 110 is delivered along the axis of the outer tube body 102 and protrudes out of the endoscope exit port 116.

The proximal end cap 104 is provided with a valve member 120. The valve member 120 seals the treatment tool entry port 108 and the endoscope entry port 110.

Figure 12:
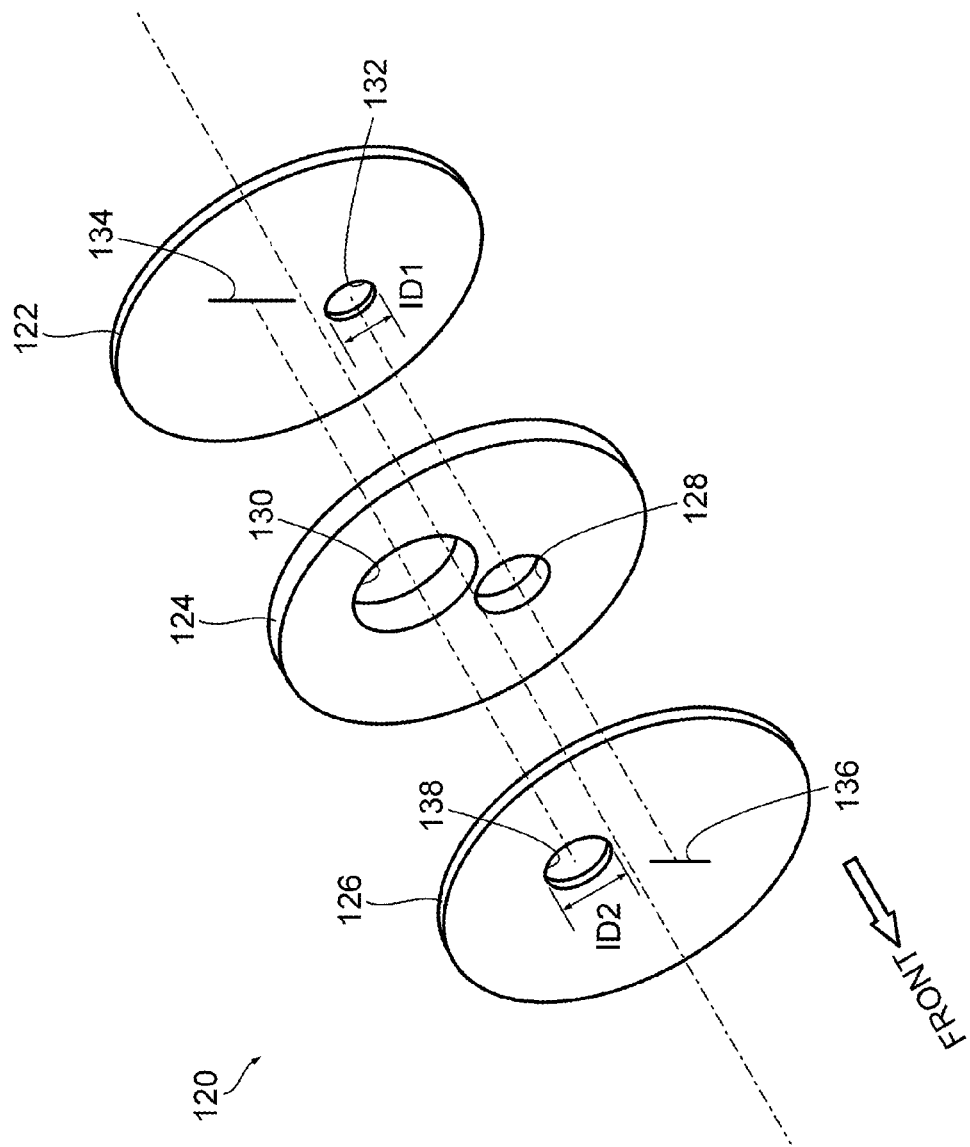
FIG. 12 is an exploded perspective view showing a schematic configuration of a valve member.
Figure 13:
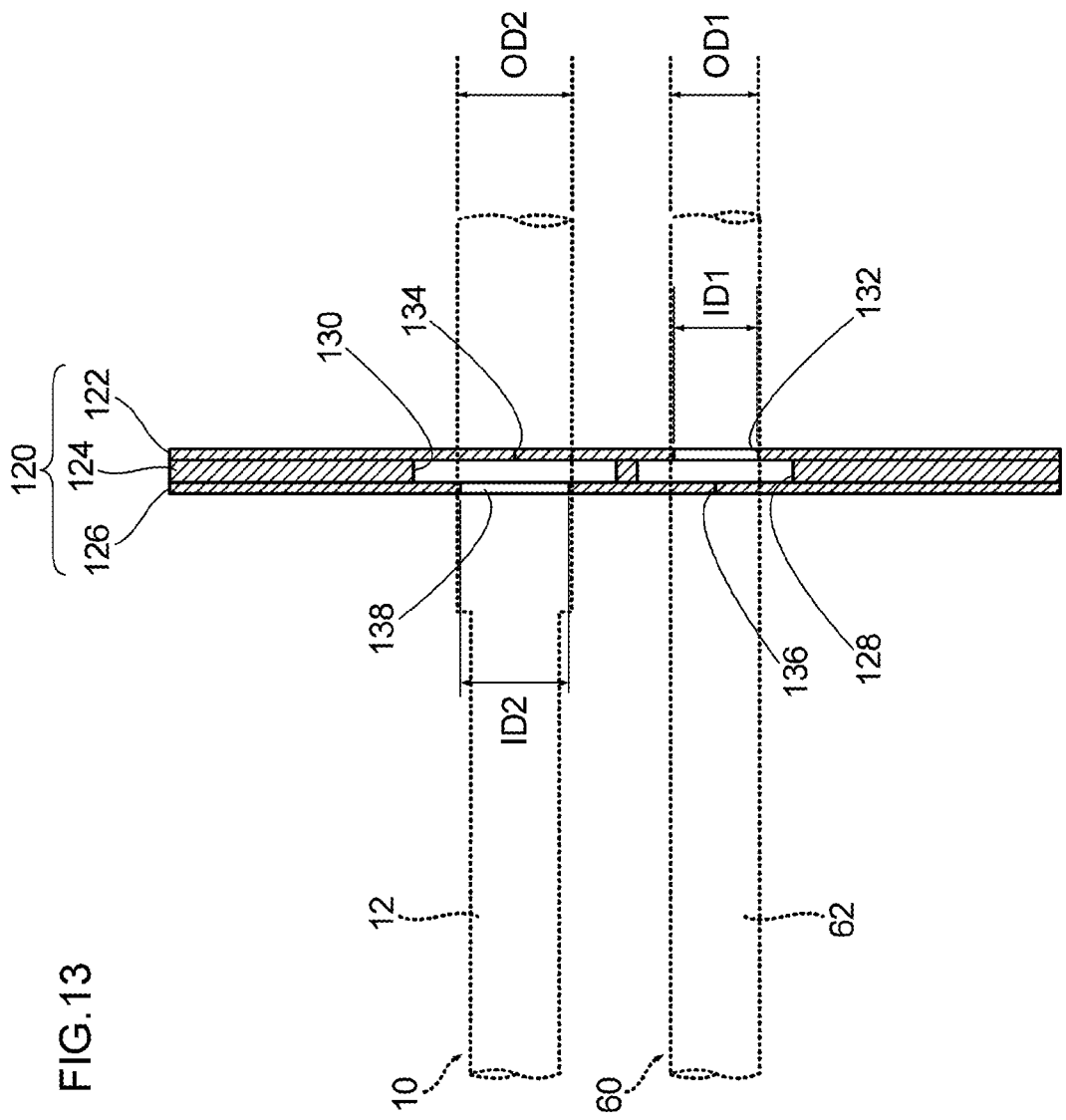
FIG. 13 is a side sectional view of the valve member.

FIG. 12 is an exploded perspective view showing a schematic configuration of the valve member. FIG. 13 is a side sectional view of the valve member.

The valve member 120 is configured to include a first valve body 122, an intermediate member 124, and a second valve body 126.

The first valve body 122, the intermediate member 124 and the second valve body 126 are circular plate members (disk-shaped members) having the same outer diameter, and coaxially overlaid on be so as to be integrated, thus configuring the valve member 120.

The first valve body 122 and the second valve body 126 are made of an elastic material, such as natural rubber, synthetic rubber, or silicone rubber, and formed to be elastically deformable.

The intermediate member 124 is made of a material having stiffness, which is metal, such as stainless steel or aluminum, or rigid plastic or the like. The intermediate member 124 has a role of reinforcing the first valve body 122 and the second valve body 126, which are overlaid on the front and rear of this member 124.

The intermediate member 124 has a treatment tool insertion hole 128 into which the insertion part 62 of the treatment tool 60 is inserted, and an endoscope insertion hole 130 into which the insertion part 12 of the endoscope 10 is inserted.

The treatment tool insertion hole 128 has a circular shape, and is formed to have a size allowing the insertion part 62 of the treatment tool 60 to be inserted into this hole. That is, this hole is formed to have a size which makes the thickest portion of the insertion part 62 of the treatment tool 60 to be inserted into the outer tube 100 insertable into the port.

The endoscope insertion hole 130 has a circular shape, is formed to have a size allowing the insertion part 12 of the endoscope 10 to be inserted into this hole. That is, this hole is formed to have a size which makes the thickest portion of the insertion part 12 of the endoscope 10 to be inserted into the outer tube 100 insertable into the port.

The treatment tool insertion hole 128 is arranged coaxially with the treatment tool entry port 108. The endoscope insertion hole 130 is arranged coaxially with the endoscope entry port 110. Consequently, when the insertion part 62 of the treatment tool 60 is inserted through the treatment tool entry port 108, the insertion part 62 of the treatment tool 60 is, in turn, inserted into the treatment tool insertion hole 128. When the insertion part 12 of the endoscope 10 is inserted through the endoscope entry port 110, the insertion part 12 of the endoscope 10 is, in turn, inserted into the endoscope insertion hole 130.

The first valve body 122 arranged on the proximal end side is provided with an opening type hermetic valve part 132 for the treatment tool, and a slit type hermetic valve part 134 for the endoscope.

The opening type hermetic valve part 132 for the treatment tool is formed as a circular opening in the first valve body 122. The opening type hermetic valve part 132 for the treatment tool functions as a sealing member (second sealing member, treatment tool sealing member) that seals a gap formed between the insertion part 62 of the treatment tool 60 and the treatment tool entry port 108 when the insertion part 62 of the treatment tool 60 is inserted into the outer tube 100. The opening type hermetic valve part 132 for the treatment tool is arranged coaxially with the treatment tool insertion hole 128. This opening type hermetic valve part 132 is formed to have an inner diameter ID1 that is slightly smaller than the outer diameter (the outer diameter of a part in contact with the opening type hermetic valve part 132 for the treatment tool) OD1 of the insertion part 62 of the treatment tool 60. Consequently, when the insertion part 62 of the treatment tool 60 is fitted into the opening type hermetic valve part 132 for the treatment tool, the inner peripheral surface of the opening is brought into close contact with the outer peripheral surface of the insertion part 62 of the treatment tool 60. Consequently, when the insertion part 62 of the treatment tool 60 is inserted into the outer tube 100, the gap formed between the insertion part 62 of the treatment tool 60 and the treatment tool entry port 108 is sealed.

The slit type hermetic valve part 134 for the endoscope is formed as a single linear slit with a predetermined length in the first valve body 122. After the insertion part 12 of the endoscope 10 is extracted out of the outer tube 100, the slit type hermetic valve part 134 for the endoscope blocks the endoscope entry port 110.

The second valve body 126, which is arranged on the distal end side, is provided with an opening type hermetic valve part 138 for the endoscope, and a slit type hermetic valve part 136 for the treatment tool.

The opening type hermetic valve part 138 for the endoscope is formed as a circular opening in the second valve body 126. When the insertion part 12 of the endoscope 10 is inserted into the outer tube 100, the opening type hermetic valve part 138 for the endoscope functions as a sealing member (first sealing member, endoscope sealing member) that seals the gap formed between the insertion part 12 of the endoscope 10 and the endoscope entry port 110. The opening type hermetic valve part 138 for the endoscope is arranged coaxially with the endoscope insertion hole 130. This opening type hermetic valve part 138 is formed to have an inner diameter ID2 that is slightly smaller than the outer diameter OD2 of the insertion part 12 of the endoscope 10. Consequently, when the insertion part 12 of the endoscope 10 is fitted into the opening type hermetic valve part 138 for the endoscope, the inner peripheral surface of the opening is brought into close contact with the outer peripheral surface of the insertion part 12 of the endoscope 10. Consequently, when the insertion part 12 of the endoscope 10 is inserted into the outer tube 100, the gap formed between the insertion part 12 of the endoscope 10 and the endoscope entry port 110 is sealed.

The slit type hermetic valve part 136 for the treatment tool is formed as a single linear slit with a predetermined length in the second valve body 126. After the insertion part 62 of the treatment tool 60 is extracted out of the outer tube 100, the slit type hermetic valve part 136 for the treatment tool, which is formed as the slit, blocks the treatment tool entry port 108.

According to the valve member 120 configured as described above, after the insertion part 62 of the treatment tool 60 and the insertion part 12 of the endoscope 10 are inserted into the outer tube 100, the hermeticity of the outer tube 100 is secured by the opening type hermetic valve part 132 for the treatment tool and the opening type hermetic valve part 138 for the endoscope. When the insertion part 62 of the treatment tool 60 and the insertion part 12 of the endoscope 10 are not inserted into the outer tube 100, the hermeticity of the outer tube 100 is secured by the slit type hermetic valve part 136 for the treatment tool and the slit type hermetic valve part 134 for the endoscope.

Inside the outer tube body 102, a slider (movable object) 140 that is movable in a direction parallel to the axis of the outer tube body 102 is provided.

The slider 140 is configured as a block that is movable in the outer tube body 102. In this embodiment, the slider is configured as a cylindrical block.

The slider 140 is configured to be movable inside the outer tube body 102 along the axis of the outer tube body 102 guided by a pair of slider guide shafts 142. The slider guide shafts 142 are each formed into a linear rod shape, and are arranged parallel to each other along the axis of the outer tube body 102. The slider guide shafts 142 are each supported by the proximal end cap 104 at the proximal end, and supported by the distal end cap 106 at the distal end, and are arranged in parallel to the axis of the outer tube body 102.

The slider 140 is provided with a pair of slider guide holes 144 into which the pair of slider guide shafts 142 can be inserted. In the pair of slider guide holes 144, the slider guide holes 144 are arranged so that the interval therebetween becomes the same as the arrangement interval of the pair of slider guide shafts 142, and are arranged in parallel to each other. The slider guide shafts 142 are inserted into the respective slider guide holes 144, thereby allowing the slider 140 to be slidably supported by the slider guide shafts 142.

The slider 140 is provided with an endoscope holding part 148 as a first holding part that holds the insertion part 12 of the endoscope 10 inserted into the outer tube body 102, and a treatment tool holding part 146 as a second holding part that holds the insertion part 62 of the treatment tool 60 inserted into the outer tube body 102.

The treatment tool holding part 146 includes a treatment tool holding hole 150 through which the insertion part 62 of the treatment tool 60 is inserted, and a cylindrical (annular) elastic member 152 that is arranged in the treatment tool holding hole 150.

The treatment tool holding hole 150 is formed to penetrate through the slider 140, and formed in parallel to the axis of the outer tube body 102. The treatment tool holding hole 150 is provided for the slider 140 so as to be arranged coaxially with the treatment tool entry port 108 and the treatment tool exit port 114.

The cylindrical elastic member 152 is coaxially fixed and attached to the inner circumference part of the treatment tool holding hole 150. The cylindrical elastic member 152 is formed to have an inner diameter ID3 that is slightly smaller than the outer diameter (the outer diameter of a part held by the treatment tool holding part 146) OD3 of the insertion part 62 of the treatment tool 60.

In the treatment tool 60 of this embodiment, the insertion part 62 has the constant outer diameter. Consequently, the outer diameter OD3 of the part held by the treatment tool holding part 146 is the same as the outer diameter OD1 of the part which is in contact with the opening type hermetic valve part 132 for the treatment tool (OD1=OD3). Accordingly, the inner diameter ID3 of the elastic member 152 is identical to or substantially identical to the inner diameter ID1 of the opening type hermetic valve part 132 for the treatment tool.

The insertion part 62 of the treatment tool 60, which is inserted from the treatment tool entry port 108 into the outer tube body 102, passes through the treatment tool holding hole 150 and is delivered to protrude out of the treatment tool exit port 114. When the insertion part 62 of the treatment tool 60 passes through the treatment tool holding hole 150, this part passes through the elastic member 152. As described above, the elastic member 152 is formed to have the inner diameter that is slightly smaller than the outer diameter (the outer diameter of the part held by the treatment tool holding part 146) of the insertion part 62 of the treatment tool 60. Consequently, when the insertion part 62 of the treatment tool 60 passes through the treatment tool holding hole 150, this part is held by the treatment tool holding hole 150 by means of the elastic force of the elastic member 152.

Note that the treatment tool 60 is thus held by means of the elastic force of the elastic member 152. Consequently, the holding position of the treatment tool 60 can be arbitrarily adjusted with respect to the slider 140.

The treatment tool 60 is held by the elastic force of the elastic member 152. However, the frictional force between the elastic member 152 and the insertion part 62 of the treatment tool 60 is configured to be higher than the frictional force between the slider guide shaft 142 and the slider guide hole 144 (=the frictional force between the outer tube body 102 and the slider 140). Consequently, when the treatment tool 60 is moved in the axial direction, the slider 140 and the treatment tool 60 are integrally moved with respect to the outer tube body 102.

The endoscope holding part 148 includes an endoscope holding hole 154 through which the insertion part 12 of the endoscope 10 is inserted, and a cylindrical (annular) elastic member 156 that is arranged in the endoscope holding hole 154.

The endoscope holding hole 154 is formed to penetrate through the slider 140, and formed in parallel to the axis of the outer tube body 102. The endoscope holding hole 154 is provided for the slider 140 so as to be arranged coaxially with the endoscope entry port 110 and the endoscope exit port 116.

The cylindrical elastic member 156 is coaxially fixed and attached to the inner circumference part of the endoscope holding hole 154. The cylindrical elastic member 156 is formed to have an inner diameter ID4 that is slightly smaller than the outer diameter (the outer diameter of a part held by the endoscope holding part 148) OD4 of the insertion part 12 of the endoscope 10.

The insertion part 12 of the endoscope 10 inserted from the endoscope entry port 110 into the outer tube body 102 passes through the endoscope holding hole 154, and is delivered to protrude out of the endoscope exit port 116. When the endoscope 10 passes through the endoscope holding hole 154, this endoscope passes through the elastic member 156. As described above, the elastic member 156 is formed to have the inner diameter that is slightly smaller than the outer diameter of the insertion part 12 of the endoscope 10. Consequently, after the insertion part 12 of the endoscope 10 passes through the endoscope holding hole 154, the insertion part 12 is held by the endoscope holding hole 154 by means of the elastic force of the elastic member 156.

Note that the endoscope 10 is thus held by means of the elastic force of the elastic member 156. Consequently, the holding position of the endoscope 10 can be arbitrarily adjusted with respect to the slider 140.

The endoscope 10 is held by the elastic force of the elastic member 156. However, the frictional force between the elastic member 156 and the insertion part 12 of the endoscope 10 is configured to be higher than the frictional force between the slider guide shaft 142 and the slider guide hole 144 (=the frictional force between the outer tube body 102 and the slider 140). Consequently, when the endoscope 10 is moved in the axial direction, the slider 140 and the endoscope 10 are integrally moved with respect to the outer tube body 102.

Note that when the endoscope 10 is inserted into the outer tube 100, this endoscope is thus inserted into the opening type hermetic valve part 138 for the endoscope provided at the valve member 120, and into the cylindrical elastic member 156 provided in the endoscope holding part 148. The opening type hermetic valve part 138 for the endoscope is formed to have the inner diameter ID2 that is larger than the inner diameter ID4 of the elastic member 156. Accordingly, in the insertion part 12 of the endoscope 10, the outer diameter OD2 (second diameter A2) of the part (the part having the second diameter A2) which is brought into contact with the opening type hermetic valve part 138 for the endoscope is formed so as to be larger than the outer diameter OD4 (first diameter A1) of the part (the part having the first diameter A1) held by the endoscope holding part 148. That is, the insertion part 12 of the endoscope 10 is formed to have a diameter varying along the longitudinal direction (axial direction) (two-step thickness in this example), and formed such that the proximal end part side is formed thicker than the distal end part side. Consequently, the insertion and extraction operation of the endoscope 10 into and from the outer tube 100 can be easily performed. That is, the distal end part side of the insertion part 12 of the endoscope 10 is formed thin, which can reduce the resistance applied from the valve member 120 during insertion and extraction. Consequently, the endoscope 10 can be smoothly inserted and extracted without unnecessary force, and the usability can be improved. Furthermore, the load applied to the valve member 120 during insertion and extraction can be reduced, and the life-span of the valve member 120 can be increased. Moreover, in the outer tube 100, the part exposed from the proximal end part is formed thick. Consequently, the endoscope becomes resistant to deformation, and direct operational feeling with high stiffness can be obtained. Furthermore, reduction in the diameter of the part held by the endoscope holding part 148 can reduce the size of the slider 140, which can, in turn, reduce the diameter of the outer tube 100 as a whole.

The part of the endoscope 10 formed to have the larger diameter is the part in contact with the opening type hermetic valve part 138 for the endoscope during usage as described above. The endoscope 10 moves in interlock with the treatment tool 60 during usage through the outer tube 100. Consequently, the part that is in contact with the opening type hermetic valve part 138 for the endoscope at least during usage is formed to have a larger diameter.

The degree of increase of the diameter is set in consideration of the sliding friction applied from the valve member 120. That is, it is sufficient to reduce the resistance applied to the distal end part side during insertion and extraction. Consequently, it is preferable to adopt the minimum thickness within a range that can achieve such an object. This adoption can facilitate narrowing the endoscope 10 and the outer tube 100.

Thus, in view with reference to the endoscope 10, the outer tube 100 includes the valve member 120 configured in conformity with the outer diameter of the endoscope 10. That is, the opening type hermetic valve part 138 for the endoscope is configured such that the thickly formed insertion part 12 on the proximal end part side can be slidably sealed, and the slit type hermetic valve part 134 for the endoscope is configured such that the endoscope entry port 110 can be sealed when the endoscope 10 is extracted.

<<Operation of Endoscopic Surgical Device>>

First, the insertion part 12 of the endoscope 10 is inserted from the endoscope entry port 110. The insertion part 12 inserted into the endoscope entry port 110 passes through the outer tube body 102, and delivered to protrude out of the endoscope exit port 116. In this case, the insertion part 12 passes through the endoscope holding hole 154 provided in the slider 140 in the outer tube body 102, and is delivered to protrude out of the endoscope exit port 116. The endoscope holding hole 154 is provided with the elastic member 156. The insertion part 12 passing through the endoscope holding hole 154 is held by the slider 140 by means of the elastic force of the elastic member 156.

Next, the insertion part 62 of the treatment tool 60 is inserted from the treatment tool entry port 108. The insertion part 62 inserted into the treatment tool entry port 108 passes through the outer tube body 102, and is delivered to protrude out of the treatment tool exit port 114. In this case, the insertion part 62 passes through the treatment tool holding hole 150 provided in the slider 140 in the outer tube body 102, and is delivered to protrude out of the treatment tool exit port 114. The treatment tool holding hole 150 is provided with the elastic member 152. The insertion part 62 passing through the treatment tool holding hole 150 is held by the slider 140 by means of the elastic force of the elastic member 152.

Both the insertion part 12 of the endoscope 10 inserted into the outer tube 100 and the insertion part 62 of the treatment tool 60 are held by the slider 140. Consequently, when the treatment tool 60 is moved in the axial direction, the endoscope 10 is moved in the axial direction in interlock with the movement.

As described above, the endoscopic surgical device 1 of this embodiment can move the endoscope 10 in interlock with the treatment tool 60. Consequently, the visual field (imaging region) of the endoscope 10 can be caused to follow the treatment part, and an image optimal to treatment can be always provided for the operator.

Note that the movement (to-and-fro movement) in the forward and rear direction of the endoscope visual field is performed by the movement in the axial direction of the treatment tool 60. Meanwhile, the movement in the vertical and horizontal directions is performed by the inclination movement of the treatment tool 60. That is, all the parts including the outer tube 100 are inclined to move the visual field.

Typically, laparoscopic surgery is performed by supplying gas into the abdominal cavity to expand the abdominal cavity. However, the outer tube 100 is provided with the valve member 120. Consequently, the hermeticity can be secured.

Furthermore, in the endoscope 10, the distal end part side of the insertion part 12 is formed thinner than the proximal end part side. Consequently, the insertion and extraction operation for the outer tube 100 can be easily performed. Furthermore, the load applied to the valve member can be reduced, and the life-span of the valve member can be increased.

<<Example of Use of Endoscopic Surgical Device>>

Figure 14:
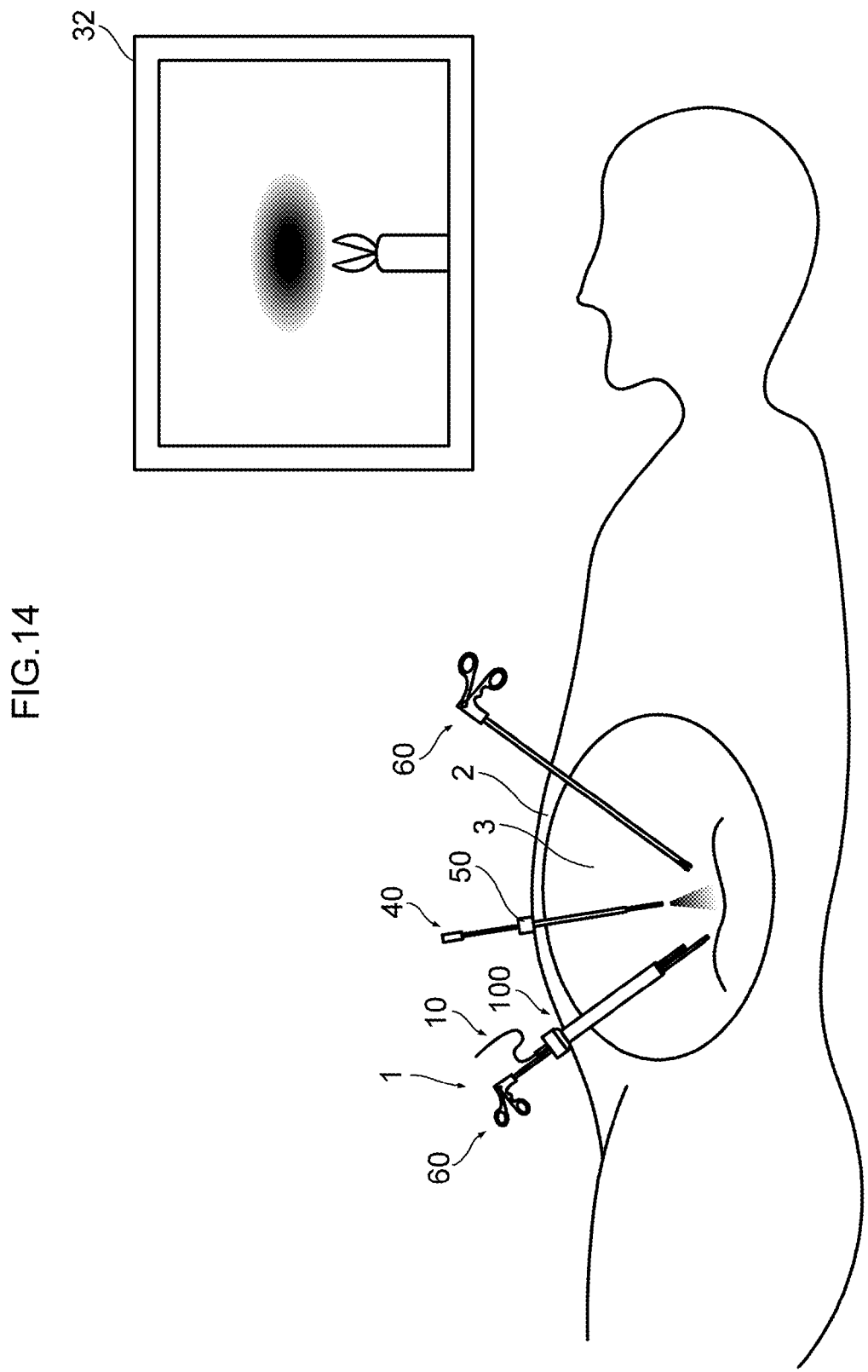
FIG. 14 is a schematic diagram showing an example of an operation method using the endoscopic surgical device.

FIG. 14 is a schematic diagram showing an example of an operation method using the endoscopic surgical device.

This example indicates an example of the case where a single operator performs treatment.

The endoscope 10 and the treatment tool 60 are inserted into the body cavity 3 through the outer tube 100 that is punctured into the body cavity wall 2 of the patient. The endoscope 10 moves in interlock with the movement of the treatment tool 60. Consequently, the video image of a site to be treated is always displayed on the monitor 32, and the movement of the treatment tool 60 can, in turn, move the visual field.

The endoscope 10 is provided with no illumination means. Consequently, the needle light 40 is used as the illumination means. The needle light 40 is inserted into the body cavity 3 through the outer tube 50 for the needle light. The body cavity 3 is illuminated with illumination light emitted from the distal end of the needle light 40. This example exemplifies the case of using the single needle light 40. Alternatively, multiple needle lights 40 may be used as necessary.

According to the endoscopic surgical device 1 of this embodiment, the operation of the treatment tool 60 also operates the endoscope 10. Consequently, treatment can be performed by a single operator. That is, laparoscopist is unnecessary.

Furthermore, the endoscope 10 and the treatment tool 60 are inserted into the body cavity 3 through the outer tube 100. Consequently, only one site to be punctured is required to insert the endoscope 10 and the treatment tool 60 into the body cavity. Therefore, a low-invasive operation can be performed.

<<Second Embodiment of Outer Tube>>

Figure 15:
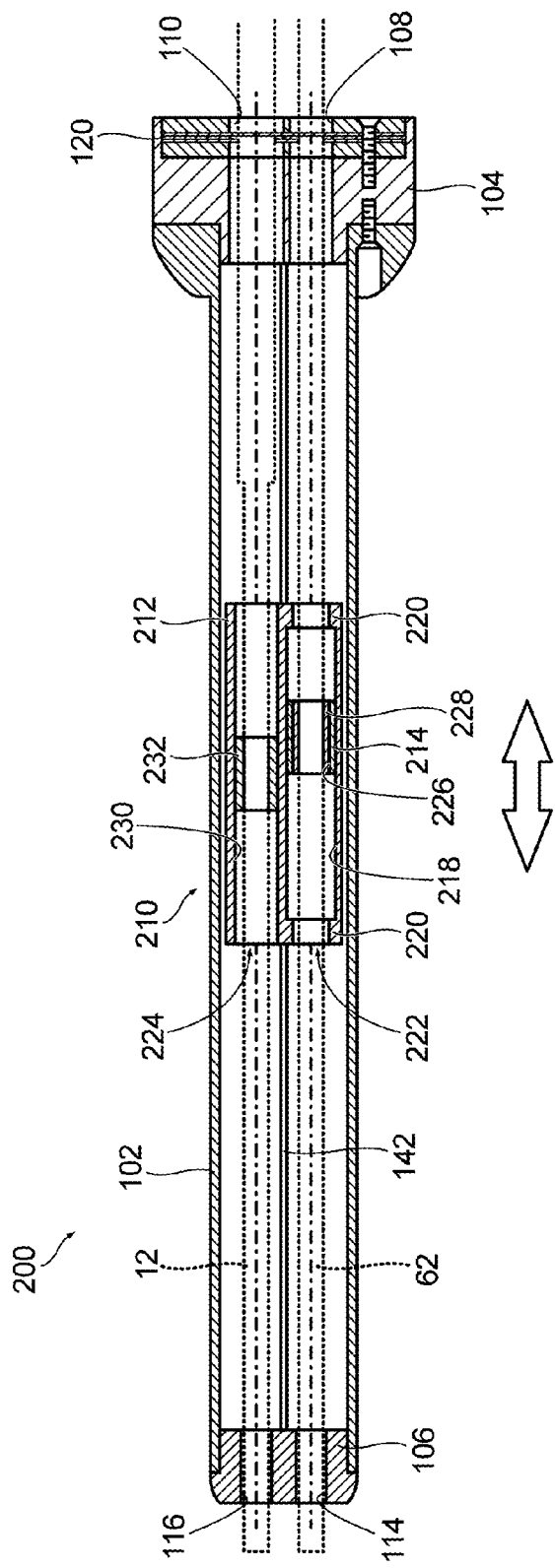
FIG. 15 is a side sectional view of an outer tube of a second embodiment.
Figure 16:
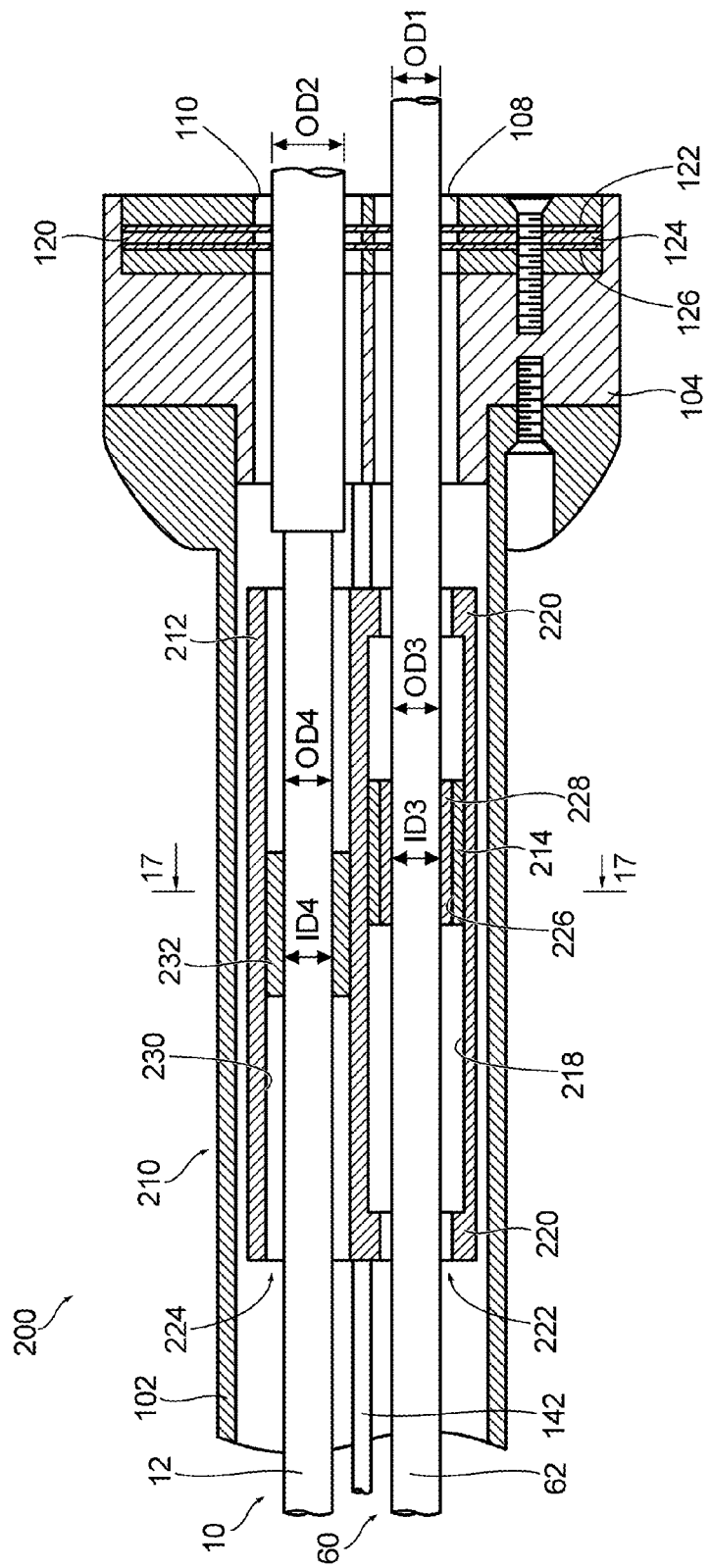
FIG. 16 is an enlarged sectional view of a proximal end part of the outer tube of the second embodiment.
Figure 17:
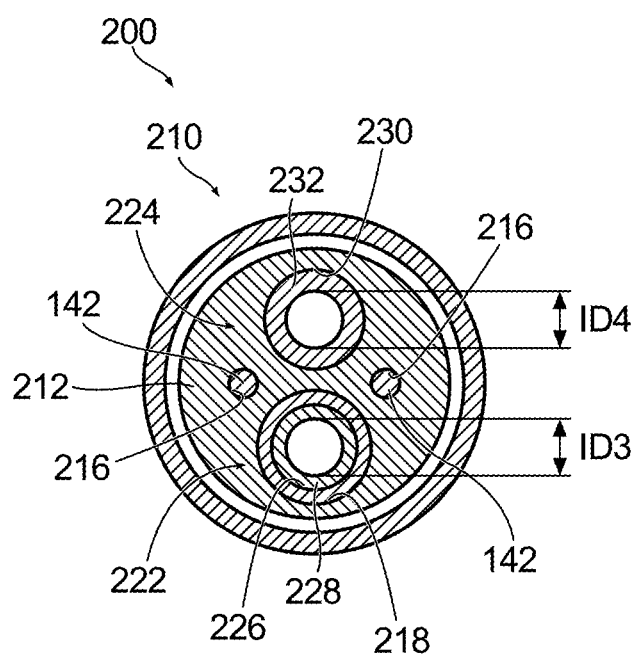
FIG. 17 is a sectional view taken along 17-17 of FIG. 16.

FIG. 15 is a side sectional view of an outer tube of a second embodiment. FIG. 16 is an enlarged sectional view of a proximal end part of the outer tube of the second embodiment. FIG. 17 is a sectional view taken along 17-17 of FIG. 16.

The outer tube 200 of this embodiment is different from the outer tube 100 of the embodiment described above in that a slider 210 arranged inside an outer tube body includes a movable part. Except for the difference in the configuration of the slider 210, the configuration is the same as the configuration of the outer tube 100 of the embodiment described above. Consequently, only the configuration of the slider 210 is herein described (the same signs are assigned to other configurations, and the explanation about them is omitted).

<Configuration>

The slider 210 is configured to include a slider body (movable object main body) 212, and a sleeve (movable part) 214 that is configured to be movable in the axial direction with respect to the slider body.

The slider body 212 is configured as a block that is movable in the outer tube body 102. In this embodiment, this body is configured as a cylindrical block.

The slider body 212 is configured to be movable inside the outer tube body 102 along the axis of the outer tube body 102 guided by the pair of slider guide shafts 142. The slider body 212 is provided with a pair of slider guide holes 216 through which the pair of slider guide shafts 142 can be inserted. The pair of slider guide holes 216 is arranged so that the interval between the slider guide holes 216 is the same as the arrangement interval of the pair of slider guide shafts 142, and the slider guide holes 216 are arranged parallel to each other. The slider guide shafts 142 are inserted into the respective slider guide holes 216, thereby allowing the slider body 212 to be slidably supported by the slider guide shafts 142.

The slider body 212 is provided with a sleeve guide hole 218. The sleeve guide hole 218 is formed to be a hole having a round-shaped cross-section and to penetrate through the slider body 212. The sleeve guide hole 218 is formed in parallel to the axis of the outer tube body 102, and provided in the slider body 212 so as to be arranged coaxially with the treatment tool entry port 108 and the treatment tool exit port 114.

The sleeve 214 is formed to have a shape (a cylindrical body in this example) that is slidable in the sleeve guide hole 218. The sleeve 214 is contained in the sleeve guide hole 218, and movably arranged in the sleeve guide hole 218. In the sleeve guide hole 218, stopper parts 220 for restricting the movement of the sleeve 214 are provided at both ends thereof so as to protrude in radial directions. The movable range of the sleeve 214 is restricted by the stopper parts 220. Furthermore, the sleeve 214 is prevented from dropping off from the sleeve guide hole 218 by the stopper parts 220.

The slider 210 is provided with a treatment tool holding part 222 that holds the insertion part 62 of the treatment tool 60 inserted into the outer tube body 102, and an endoscope holding part 224 that holds the insertion part 12 of the endoscope 10 inserted into the outer tube body 102. The treatment tool holding part 222 is provided in the sleeve 214. The endoscope holding part 224 is provided in the slider body 212.

The treatment tool holding part 222 includes a treatment tool holding hole 226 through which the insertion part 62 of the treatment tool 60 is inserted, and a cylindrical (annular) elastic member 228 arranged in the treatment tool holding hole 226.

The treatment tool holding hole 226 is configured by the inner circumference part of the sleeve 214, which is configured to be a cylindrical body. As described above, the sleeve guide hole 218 that guides the sleeve 214 is formed in parallel to the axis of the outer tube body 102, and arranged coaxially with the treatment tool entry port 108 and the treatment tool exit port 114. Consequently, the treatment tool holding hole 226, which is the inner circumference part of the sleeve 214, is also arranged in parallel to the axis of the outer tube body 102, and arranged coaxially with the treatment tool entry port 108 and the treatment tool exit port 114.

The cylindrical elastic member 228 is coaxially fixed and attached to the inner circumference part of the treatment tool holding hole 226. The cylindrical elastic member 228 is formed to have the inner diameter ID3 that is slightly smaller than the outer diameter (the outer diameter of the part held by treatment tool holding part 222) OD3 of the insertion part 62 of the treatment tool 60.

The insertion part 62 of the treatment tool 60 inserted from the treatment tool entry port 108 into the outer tube body 102 passes through the treatment tool holding hole 226, and is delivered to protrude out of the treatment tool exit port 114. When the insertion part 62 of the treatment tool 60 passes through the treatment tool holding hole 226, this part passes through the elastic member 228. As described above, the elastic member 228 is formed to have the inner diameter that is slightly smaller than the outer diameter (the outer diameter of the part held by the treatment tool holding part 222) of the insertion part 62 of the treatment tool 60. Consequently, after the insertion part 62 of the treatment tool 60 passes through the treatment tool holding hole 226, this part is held by the treatment tool holding hole 226 by means of the elastic force of the elastic member 228.

Note that the part is thus held by means of the elastic force of the elastic member 228. Consequently, the holding position of the treatment tool 60 can be arbitrarily adjusted with respect to the sleeve 214.

The endoscope holding part 224 includes an endoscope holding hole 230 through which the insertion part 12 of the endoscope 10 is inserted, and a cylindrical (annular) elastic member 232 arranged in the endoscope holding hole 230.

The endoscope holding hole 230 is formed to penetrate through the slider body 212, and formed in parallel to the axis of the outer tube body 102. The endoscope holding hole 230 is provided for the slider body 212 so as to be arranged coaxially with the endoscope entry port 110 and the endoscope exit port 116.

The cylindrical elastic member 232 is coaxially fixed and attached to the inner circumference part of the endoscope holding hole 230. The cylindrical elastic member 232 is formed to have the inner diameter ID4 that is slightly smaller than the outer diameter (the outer diameter of the part held by the endoscope holding part 224) OD4 of the insertion part 12 of the endoscope 10.

The insertion part 12 of the endoscope 10 inserted from the endoscope entry port 110 into the outer tube body 102 passes through the endoscope holding hole 230, and is delivered to protrude out of the endoscope exit port 116. When the endoscope 10 passes through the endoscope holding hole 230, the endoscope 10 passes through the elastic member 232. As described above, the elastic member 232 is formed to have the inner diameter that is slightly smaller than the outer diameter of the insertion part 12 of the endoscope 10. Consequently, after the insertion part 12 of the endoscope 10 passes through the endoscope holding hole 230, this part is held by the endoscope holding hole 230 by means of the elastic force of the elastic member 232.

Note that the part is thus held by means of the elastic force of the elastic member 232. Consequently, the holding position of the endoscope 10 can be arbitrarily adjusted with respect to the slider body 212.

The outer tube 200 of this embodiment is configured as described above.

Note that this outer tube is the same as the outer tube 100 of the embodiment described above in that the opening type hermetic valve part 138 for the endoscope provided in the valve member 120 is formed to have the inner diameter ID2 that is larger than the inner diameter ID4 of the elastic member 232 provided in the endoscope holding part 224 of the slider body 212.

Consequently, in the endoscope 10 used in the outer tube 200 of this embodiment, the outer diameter OD2 of the part that is in contact with the opening type hermetic valve part 138 for the endoscope is formed to be larger than the outer diameter OD4 of the part held by the endoscope holding part 224. Consequently, the insertion and extraction operation of the endoscope 10 can be easily performed.

<Operation>

First, the insertion part 12 of the endoscope 10 is inserted from the endoscope entry port 110. The insertion part 12 inserted into the endoscope entry port 110 passes through the outer tube body 102, and is delivered to protrude out of the endoscope exit port 116. In this case, the insertion part 12 passes through the endoscope holding hole 230 provided in the slider 210 in the outer tube body 102, and is delivered to protrude out of the endoscope exit port 116. The endoscope holding hole 230 is provided with the elastic member 232. The insertion part 12 passing through the endoscope holding hole 230 is held by the slider body 212 by means of the elastic force of the elastic member 232.

Next, the insertion part 62 of the treatment tool 60 is inserted from the treatment tool entry port 108. The insertion part 62 inserted into the treatment tool entry port 108 passes through the outer tube body 102, and is delivered to protrude out of the treatment tool exit port 114. In this case, the insertion part 62 passes through the inner circumference part (treatment tool holding hole 226) of the sleeve 214 provided in the slider 210 in the outer tube body 102, and is delivered to protrude out of the treatment tool exit port 114. The inner circumference part (treatment tool holding hole 226) of the sleeve 214 is provided with the elastic member 228. The insertion part 62 passing through the inner circumference part (treatment tool holding hole 226) of the sleeve 214 is held by the sleeve 214 by means of the elastic force of the elastic member 228.

After the insertion part 12 of the endoscope 10 and the insertion part 62 of the treatment tool 60 are thus inserted into the outer tube 200, the insertion part 12 of the endoscope 10 and the insertion part 62 of the treatment tool 60 are connected by the slider 210. As a result, when the treatment tool 60 is moved in the axial direction, the endoscope 10 is moved in the axial direction in interlock with the movement.

Here, the sleeve 214 for holding the treatment tool 60 is configured to be movable in the axial direction with respect to the slider body 212 for holding the endoscope 10. As a result, only when the treatment tool 60 is moved by a predetermined amount or more, the endoscope 10 moves in interlock with the treatment tool 60. That is, even when the treatment tool 60 is moved, if the movement of the tool is within the movable range of the sleeve 214, the endoscope 10 is not moved and its stationary state is maintained. On the other hand, when the treatment tool 60 is moved exceeding the movable range of the sleeve 214, the endoscope 10 is moved in interlock with the movement of the treatment tool 60. That is, the interlocked movement is not caused by minute and small movement. Instead, the interlocked movement is caused only by large movement.

The movable range of the treatment tool 60 is restricted by the stopper parts 220 at both the ends of the sleeve guide hole 218. Consequently, when the sleeve 214 abuts on the stopper part 220, the treatment tool 60 and the endoscope 10 move in interlock with each other.

Thus, the outer tube 200 of this embodiment is provided with so-called a play (non-sensitive region) for the movement of the treatment tool 60, and is configured so as not to transmit small movement to the endoscope 10. Consequently, even when the insertion part 62 of the treatment tool 60 is minutely displaced in the axial direction (the case of performing to-and-fro movement with a small amplitude), the image on the screen can be prevented from swaying (a stable image can be provided).

If the frictional force between the sleeve 214 and the sleeve guide hole 218 is greater than the frictional force between the slider guide shaft 142 and the slider guide hole 216 (=the frictional force between the outer tube body 102 and the slider body 212), the entire slider body 212 is moved by movement of the treatment tool 60 (the sleeve 214 does not slide against the slider body 212, but the entire slider body 212 moves). Thus, the slider 210 is configured to have the frictional force between the sleeve 214 and the sleeve guide hole 218 that is smaller than the frictional force between the slider guide shaft 142 and the slider guide hole 216.

The treatment tool 60 is held by the treatment tool holding part 222 by means of the elastic force of the elastic member 228. However, the frictional force between the elastic member 228 and the insertion part 62 of the treatment tool 60 is configured to be greater than the frictional force between the sleeve 214 and the sleeve guide hole 218 and the frictional force between the slider guide shaft 142 and the slider guide hole 216 (=the frictional force between the outer tube body 102 and the slider body 212).

Likewise, the endoscope 10 is held by the endoscope holding part 224 by means of the elastic force of the elastic member 232. However, the frictional force between the elastic member 232 and the insertion part 62 of the treatment tool 60 is configured to be greater than the frictional force between the sleeve 214 and the sleeve guide hole 218 and the frictional force between the slider guide shaft 142 and the slider guide hole 216 (=the frictional force between the outer tube body 102 and the slider body 212).

<<Other Embodiments of Outer Tube>>

Figure 18:
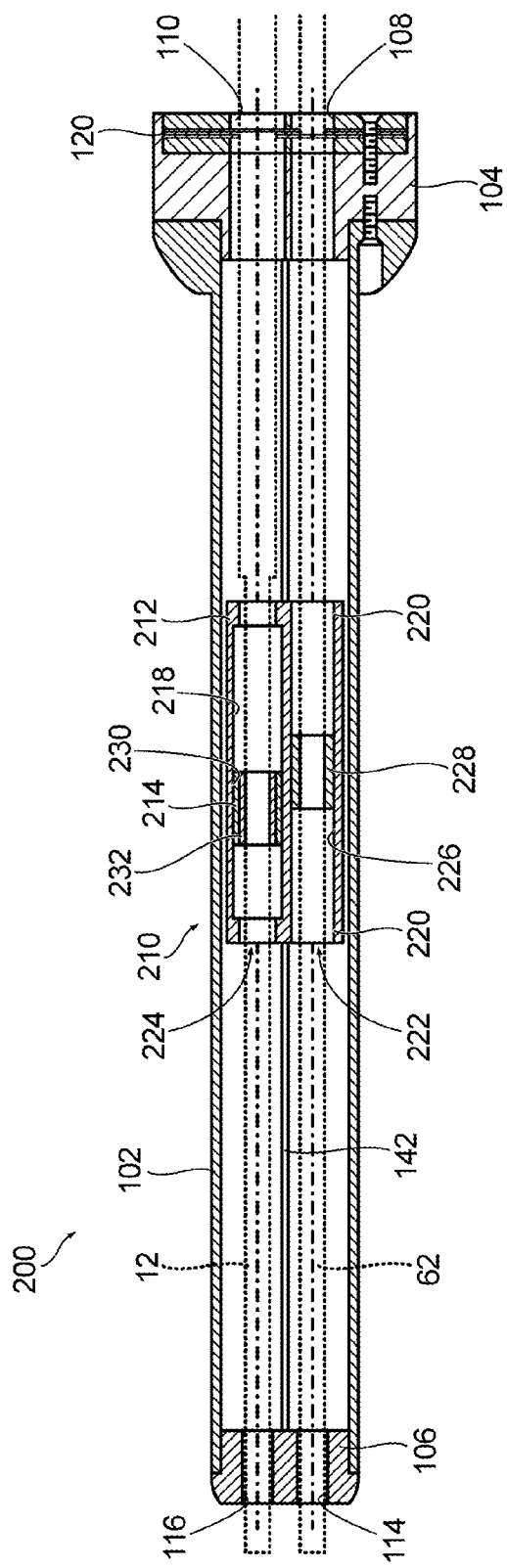
FIG. 18 is a side sectional view of an outer tube of another embodiment.

The outer tube 200 of the second embodiment has the configuration where the movable part (sleeve 214) of the slider 210 is provided with the treatment tool holding part 222, and the slider body 212 is provided with the endoscope holding part 224. Alternatively, as shown in FIG. 18, the movable part (sleeve 214) of the slider 210 may be provided with the endoscope holding part 224, and the slider body 212 may be provided with the treatment tool holding part 222. In this case, the treatment tool holding hole 226 is formed in the slider body 212, and the inner circumference part of the sleeve 214 serves as the endoscope holding hole 230. Also with such a configuration, the treatment tool 60 and the endoscope 10 can move in interlock with each other, and minute vibrations are prevented from being transmitted.

In the above embodiment, only for the endoscope, the diameter of the proximal end part side is increased (for the outer tubes 100 and 200, the inner diameter ID2 of the opening type hermetic valve parts 138 for the endoscopes is configured larger than the inner diameters ID4 of the elastic members 156 and 232). Likewise, also for the treatment tool, the diameter of the proximal end side may be increased (the outer diameter of the part that is to be in contact with the opening type hermetic valve part 132 for the treatment tool is configured larger than each of the outer diameters of the parts to be held by the treatment tool holding parts 146 and 222).

Figure 19:
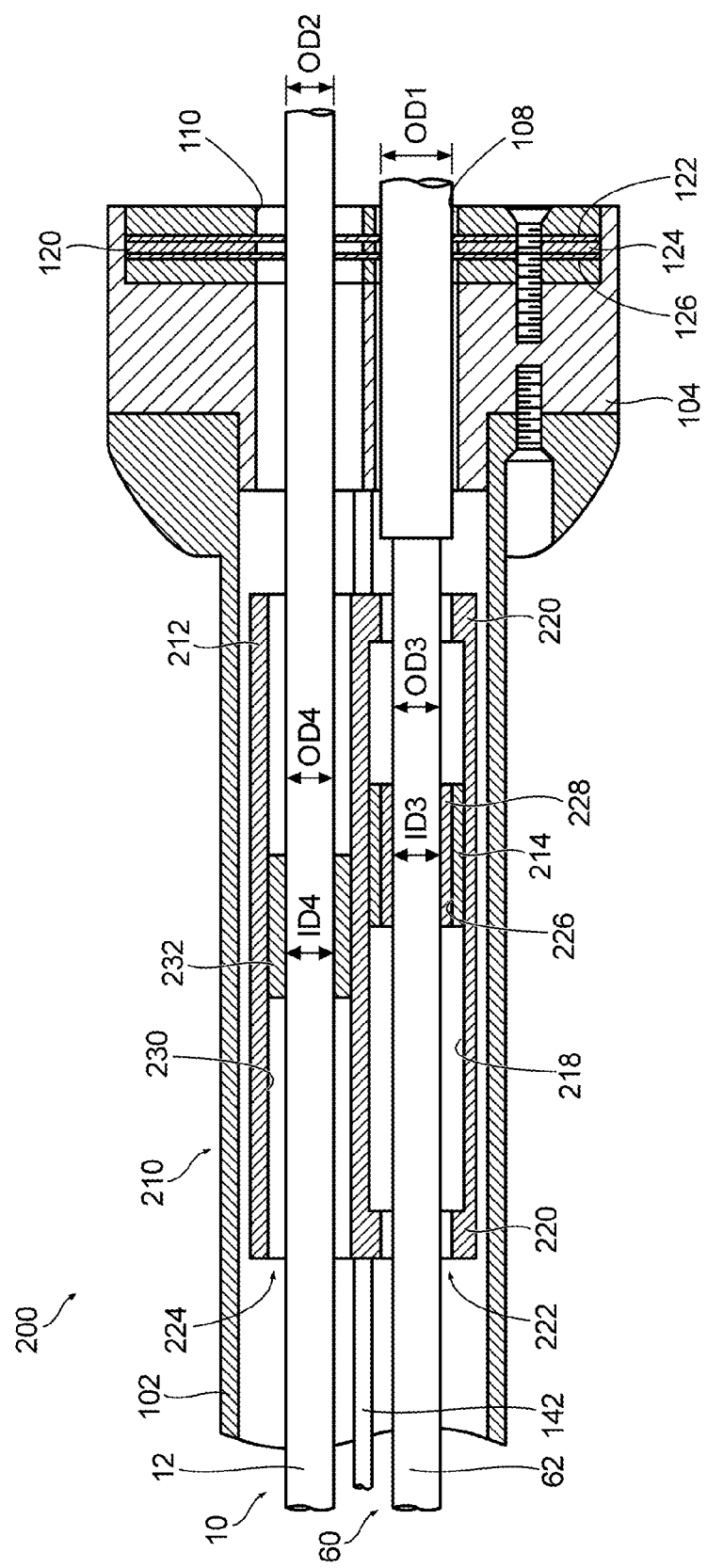
FIG. 19 is an enlarged sectional view of a proximal end part of the outer tube of the other embodiment.

In this case, in the outer tube 200, the inner diameter ID1 of the opening type hermetic valve part 132 for the treatment tool is configured to be larger than the inner diameter ID3 of the elastic member 228 as shown in FIG. 19.

On the other hand, the treatment tool 60 is configured such that the part that is to be in contact with the opening type hermetic valve part 132 for the treatment tool is formed to have the outer diameter larger than the outer diameter of the part to be held by the treatment tool holding part 222. That is, the distal end part side is formed narrower than the proximal end part side. Consequently, the insertion and extraction operation of the treatment tool 60 can be easily performed.

Here, for both the endoscope and the treatment tool, the diameters of the proximal end part sides may be increased. Alternatively, for only one of the endoscope and the treatment tool, the diameter of the proximal end part side may be increased.

In the above embodiment, only the proximal end part side of the insertion part of the endoscope 10 is formed thick. Alternatively, the diameter of the insertion part of the endoscope 10 can be varied between multi-steps. This variation is also applicable to the case of varying the diameter of the insertion part of the treatment tool.

Figure 20:
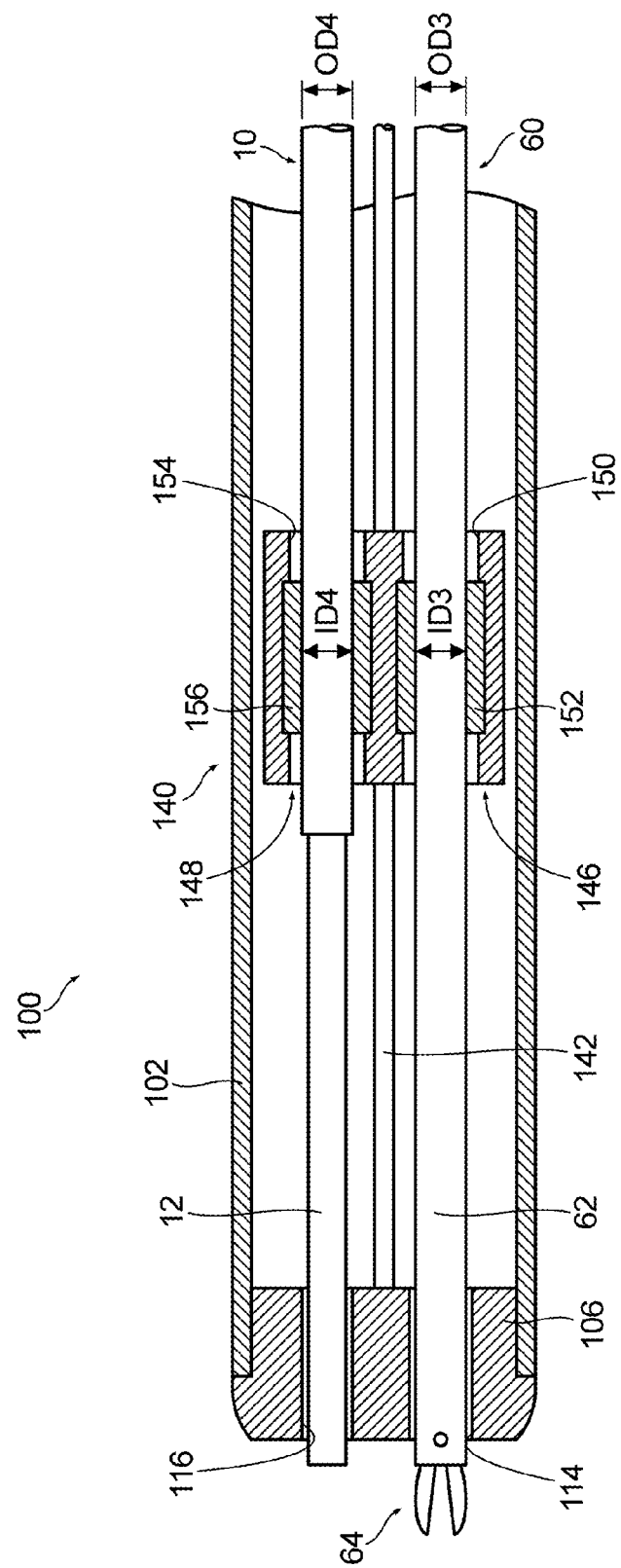
FIG. 20 is an enlarged view where a main part of an endoscope of another embodiment is enlarged.

For example, as shown in FIG. 20, the part (the part having the third diameter A3) delivered to protrude out of the endoscope exit port 116 may be formed to have the diameter (third diameter A3) that is smaller than the diameter (first diameter A1) of the part (the part having the first diameter A1) held by the endoscope holding part 148. That is, the distal end part (the part closer to the distal end than the part held by the endoscope holding part 148) of the insertion part 12 may be further narrowly formed. Consequently, it is possible to reduce the resistance applied to the distal end part of the insertion part 12 from the valve member 120 and the endoscope holding part 148 during insertion of the endoscope 10 into the outer tube 100. The reduction can further facilitate the insertion and extraction operation of the endoscope 10.

Figure 21:
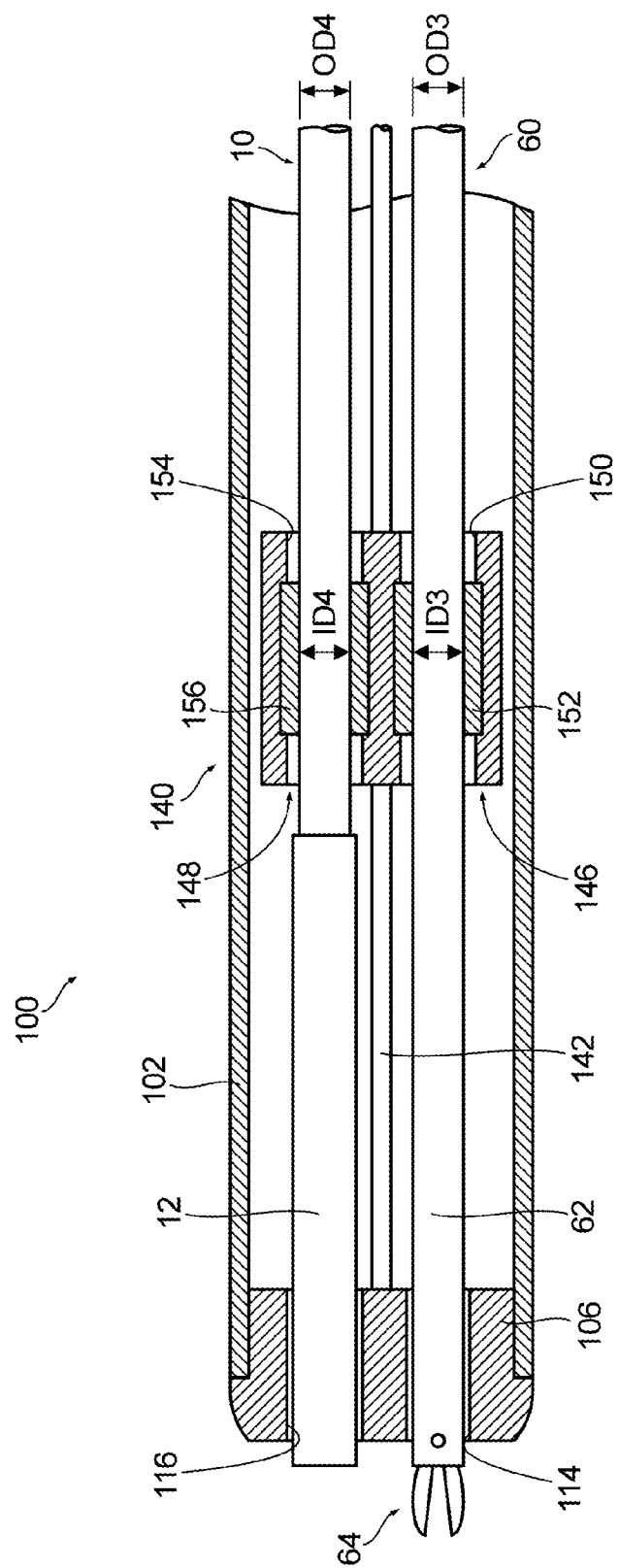
FIG. 21 is an enlarged view where a main part of an endoscope of another embodiment is enlarged.

Furthermore, as shown in FIG. 21, the part (the part having the third diameter A3) delivered to protrude out of the endoscope exit port 116 may be formed to have the diameter (third diameter A3) that is larger than the diameter (first diameter A1) of the part (the part having the first diameter A1) held by the endoscope holding part 148. That is, the distal end part (the part closer to the distal end than the part held by the endoscope holding part 148) of the insertion part 12 may be thickly formed again.

Figure 22:
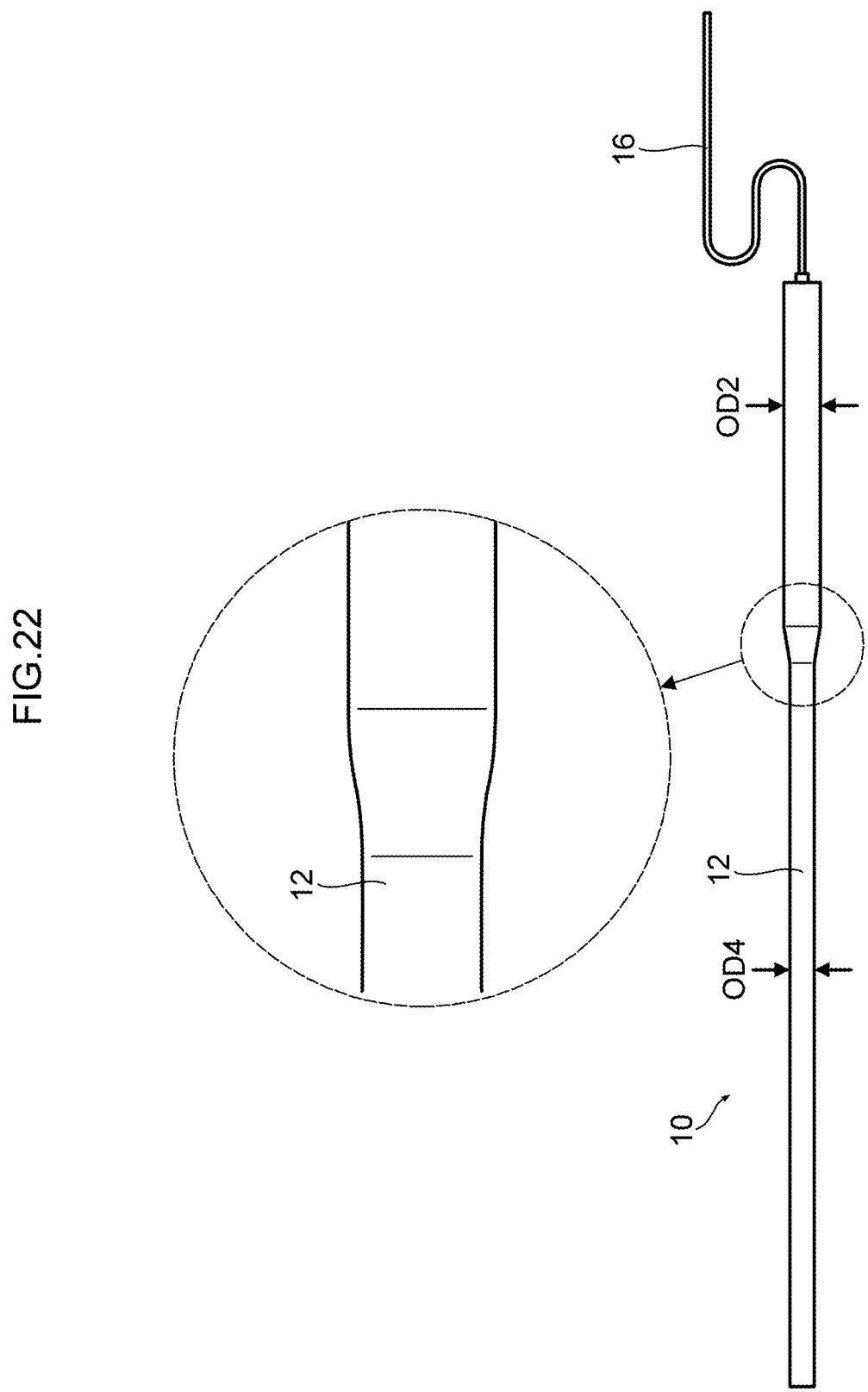
FIG. 22 is a schematic configuration diagram of a main part of an endoscope of another embodiment.

Here, in the above embodiment, in the case of varying the diameter of the insertion part of the endoscope 10, the variation is stepwisely configured. However, it is preferable that the outer diameter be smoothly varied. For example, it is preferable the variation be performed in a tapered manner, or in a curved manner as shown in FIG. 22. Consequently, during insertion and extraction of the endoscope 10, the part with a varying diameter can be prevented from being caught by the valve member 120 or the like, and insertion and extraction operation can be further smoothed. The load onto the valve member 120 can be further reduced, thereby facilitating increase in the life-span of the valve member 120.

In the above embodiments, in the endoscope holding part, the member for holding the endoscope is the cylindrical elastic member. However, in the endoscope holding part, the member for holding the endoscope is not limited to the case. Alternatively, for example, a configuration where a ring-shaped elastic member, such as an O-ring, is used to hold the endoscope may be adopted. In this case, a configuration where multiple ring-shaped elastic members are coaxially arranged to hold the endoscope may be adopted. This configuration is also applicable to the treatment tool holding part. The configuration where a ring-shaped elastic member, such as an O-ring, is used to hold the treatment tool may be adopted.

APPENDIX (A1) The surgical device, wherein the endoscope internally includes an imaging device at a distal end of the insertion part.

(A2) The surgical device, wherein the first medical instrument is a treatment tool.

(A3) The surgical device, wherein the first holding part can adjust a holding position of the insertion part of the first medical instrument.

(A4) The surgical device, wherein the second holding part can adjust a holding position of the insertion part of the second medical instrument.

(A5) The surgical device, wherein the movable object main body is configured to have a greater movement resistance to the outer tube body than a movement resistance of the movable part to the movable object main body.

(B1) The outer tube, wherein the first medical instrument is an endoscope.

(B2) The outer tube, wherein the endoscope is an endoscope that internally includes an imaging device at a distal end of the insertion part.

(B3) The outer tube, wherein the first medical instrument is a treatment tool.

(B4) The outer tube, wherein the first holding part can adjust a holding position of the insertion part of the first medical instrument.

(B5) The outer tube, wherein the second holding part can adjust a holding position of the insertion part of the second medical instrument.

(B6) The outer tube, wherein
the first sealing member has a hole and is configured by a plate-shaped elastic body,
the first holding part includes an annular elastic member through which the insertion part of the first medical instrument is inserted, and the hole of the first sealing member is configured to have a diameter that is larger than an inner diameter of the elastic member of the first holding part.

(B7) The outer tube, wherein the movable object main body is configured to have a greater movement resistance to the outer tube body than a movement resistance of the movable part to the movable object main body.

(C1) The endoscope, wherein an imaging device is internally included at a distal end of the insertion part.

(D1) The treatment tool, wherein.
the insertion part further includes a part which is disposed closer to a distal end than the part having the first diameter B1, and is configured to be delivered to protrude out of the treatment tool exit port, and has a third diameter B3 smaller than the first diameter B1.

(D2) The treatment tool, wherein
the insertion part further includes a part which is disposed closer to a distal end than the part having the first diameter B1, and is configured to be delivered to protrude out of the treatment tool exit port, and has a third diameter B3 larger than the first diameter B1.

What is claimed is:

1. A surgical device comprising: a first medical instrument that includes an insertion part; a second medical instrument that includes an insertion part; and an outer tube into which the insertion part of the first medical instrument and the insertion part of the second medical instrument are inserted, and is configured to guide the insertion part of the first medical instrument and the insertion part of the second medical instrument into a body cavity, wherein
the outer tube comprises:
a cylindrical outer tube body into which the insertion part of the first medical instrument and the insertion part of the second medical instrument are inserted;
a first entry port provided at a proximal end part of the outer tube body;
a second entry port provided at the proximal end part of the outer tube body;
a first sealing member which is provided at the first entry port and configured to slidably seal the insertion part of the first medical instrument;
a second sealing member which is provided at the second entry port and configured to slidably seal the insertion part of the second medical instrument;
a first exit port provided at a distal end part of the outer tube body;
a second exit port provided at the distal end part of the outer tube body;
a movable object which is arranged in the outer tube body and is configured to be movable in the outer tube body in an axial direction;
a first holding part which is provided at the movable object and configured to hold the insertion part of the first medical instrument inserted into the outer tube body; and
a second holding part which is provided at the movable object and configured to hold the insertion part of the second medical instrument inserted into the outer tube body, and
the insertion part of the first medical instrument comprises:
a part which is to be held by the first holding part and has a first diameter A1; and
a part which is disposed closer to a proximal end than the part having the first diameter A1, and is configured to maintain hermeticity with the first sealing member, and has a second diameter A2 being larger than the first diameter A1.

2. The surgical device according to claim 1, wherein
the insertion part of the second medical instrument comprises:
a part which is to be held by the second holding part and has a first diameter B1; and
a part which is disposed closer to a proximal end than the part having the first diameter B1, and is configured to maintain hermeticity with the second sealing member, and has a second diameter B2 being larger than the first diameter B1.

3. The surgical device according to claim 2, wherein
the insertion part of the second medical instrument further includes a part which is disposed closer to a distal end than the part having the first diameter B1, and is configured to be delivered to protrude out of the second exit port, and has a third diameter B3 smaller than the first diameter B1.

4. The surgical device according to claim 2, wherein
the insertion part of the second medical instrument further includes a part which is disposed closer to a distal end than the part having the first diameter B1, and is configured to be delivered to protrude out of the second exit port, and has a third diameter B3 larger than the first diameter B1.

5. The surgical device according to claim 1, wherein the first medical instrument is an endoscope.

6. The surgical device according to claim 1, wherein
the first sealing member has a hole and is configured by a plate-shaped elastic body,
the first holding part includes an annular elastic member through which the insertion part of the first medical instrument is inserted, and
the hole of the first sealing member is configured to have a diameter that is larger than an inner diameter of the elastic member of the first holding part.

7. The surgical device according to claim 1, wherein
the movable object comprises:
a movable object main body configured to be movable with respect to the outer tube body in the axial direction; and
a movable part configured to be movable with respect to the movable object main body in the axial direction, and
one of the first holding part and the second holding part is provided in the movable part, and another one of the first holding part and the second holding part is provided in the movable object main body.

8. The surgical device according to claim 1, wherein
the insertion part of the first medical instrument further includes a part which is disposed closer to a distal end than the part having the first diameter A1, and is configured to be delivered to protrude out of the first exit port, and has a third diameter A3 smaller than the first diameter A1.

9. The surgical device according to claim 1, wherein
the insertion part of the first medical instrument further includes a part which is disposed closer to a distal end than the part having the first diameter A1, and is configured to be delivered to protrude out of the first exit port, and has a third diameter A3 larger than the first diameter A1.

10. An outer tube into which an insertion part of a first medical instrument and an insertion part of a second medical instrument are inserted, and is configured to guide the insertion part of the first medical instrument and the insertion part of the second medical instrument into a body cavity, the outer tube comprising:
   a cylindrical outer tube body into which the insertion part of the first medical instrument and the insertion part of the second medical instrument are inserted;
   a first entry port provided at a proximal end part of the outer tube body;
   a second entry port provided at the proximal end part of the outer tube body;
   a first sealing member which is provided at the first entry port and configured to slidably seal the insertion part of the first medical instrument;
   a second sealing member which is provided at the second entry port and configured to slidably seal the insertion part of the second medical instrument;
   a first exit port provided at a distal end part of the outer tube body;
   a second exit port provided at the distal end part of the outer tube body;
   a movable object which is arranged in the outer tube body and configured to be movable in the outer tube body in an axial direction;
   a first holding part which is provided at the movable object and configured to hold the insertion part of the first medical instrument inserted into the outer tube body; and
   a second holding part which is provided at the movable object and configured to hold the insertion part of the second medical instrument inserted into the outer tube body, wherein
   the insertion part of the first medical instrument comprises:
   a part which is to be held by the first holding part and has a first diameter A1; and
   a part which is disposed closer to a proximal end than the part having the first diameter A1, and is configured to maintain hermeticity with the first sealing member, and has a second diameter A2 larger than the first diameter A1.

11. The outer tube according to claim 10, wherein the insertion part of the second medical instrument comprises:
   a part which is to be held by the second holding part and has a first diameter B1; and
   a part which is disposed closer to a proximal end than the part having the first diameter B1, and is configured to maintain hermeticity with the second sealing member, and has a second diameter B2 being larger than the first diameter B1.

12. The outer tube according to claim 11, wherein the insertion part of the second medical instrument further includes a part which is disposed closer to a distal end than the part having the first diameter B1, and is configured to be delivered to protrude out of the second exit port, and has a third diameter B3 smaller than the first diameter B1.

13. The outer tube according to claim 11, wherein the insertion part of the second medical instrument further includes a part which is disposed closer to a distal end than the part having the first diameter B1, and is configured to be delivered to protrude out of the second exit port, and has a third diameter B3 larger than the first diameter B1.

14. The outer tube according to claim 10, wherein the movable object comprises:
   a movable object main body configured to be movable with respect to the outer tube body in the axial direction; and
   a movable part configured to be movable with respect to the movable object main body in the axial direction, and
   one of the first holding part and the second holding part is provided in the movable part, and another one of the first holding part and the second holding part is provided in the movable object main body.

15. The outer tube according to claim 10, wherein the insertion part of the first medical instrument further includes a part which is disposed closer to a distal end than the part having the first diameter A1, and is configured to be delivered to protrude out of the first exit port, and has a third diameter A3 smaller than the first diameter A1.

16. The outer tube according to claim 10, wherein the insertion part of the first medical instrument further includes a part which is disposed closer to a distal end than the part having the first diameter A1, and is configured to be delivered to protrude out of the first exit port, and has a third diameter A3 larger than the first diameter A1.

17. An endoscope to be inserted into a body cavity through an outer tube which comprises: a cylindrical outer tube body into which an insertion part of an endoscope and an insertion part of a treatment tool are inserted; an endoscope entry port provided at a proximal end part of the outer tube body; a treatment tool entry port provided at the proximal end part of the outer tube body; an endoscope sealing member which is provided at the endoscope entry port and configured to slidably seal the insertion part of the endoscope; a treatment tool sealing member which is provided at the treatment tool entry port and configured to slidably seal the insertion part of the treatment tool; an endoscope exit port provided at a distal end part of the outer tube body; a treatment tool exit port provided at the distal end part of the outer tube body; a movable object which is arranged in the outer tube body and configured to be movable in the outer tube body in an axial direction; an endoscope holding part which is provided at the movable object and configured to hold the insertion part of the endoscope inserted into the outer tube body; and a treatment tool holding part which is provided at the movable object and configured to hold the insertion part of the treatment tool inserted into the outer tube body, wherein
   the insertion part comprises:
   a part which is to be held by the endoscope holding part and has a first diameter A1; and
   a part which is disposed closer to a proximal end than the part having the first diameter A1, and is configured to maintain hermeticity with the endoscope sealing member, and has a second diameter A2 larger than the first diameter A1.

18. The endoscope according to claim 17, wherein the insertion part further includes a part which is disposed closer to a distal end than the part having the first diameter A1, and is configured to be delivered to protrude out of the endoscope exit port, and has a third diameter A3 smaller than the first diameter A1.

19. The endoscope according to claim 17, wherein the insertion part further includes a part which is disposed closer to a distal end than the part having the first diameter A1, and is configured to be delivered to protrude out of the endoscope exit port, and has a third diameter A3 larger than the first diameter A1.

20. A treatment tool to be inserted into a body cavity through an outer tube which comprises: a cylindrical outer tube body into which an insertion part of an endoscope and an insertion part of a treatment tool are inserted; an endoscope entry port provided at a proximal end part of the outer tube body; a treatment tool entry port provided at the proximal end part of the outer tube body; an endoscope sealing member which is provided at the endoscope entry port and configured to slidably seal the insertion part of the endoscope; a treatment tool sealing member which is provided at the treatment tool entry port and configured to slidably seal the insertion part of the treatment tool; an endoscope exit port provided at a distal end part of the outer tube body; a treatment tool exit port provided at the distal end part of the outer tube body; a movable object which is arranged in the outer tube body and configured to be movable in the outer tube body in an axial direction; an endoscope holding part which is provided at the movable object and configured to hold the insertion part of the endoscope inserted into the outer tube body; and a treatment tool holding part which is provided at the movable object and configured to hold the insertion part of the treatment tool inserted into the outer tube body, wherein
the insertion part comprises:
a part which is to be held by the treatment tool holding part and has a first diameter B1; and
a part which is disposed closer to a proximal end than the part having the first diameter B1, and is configured to maintain hermeticity with the treatment tool sealing member, and has a second diameter B2 larger than the first diameter B1.

21. A surgical device comprising: a first medical instrument that includes an insertion part; a second medical instrument that includes an insertion part; and an outer tube into which the insertion part of the first medical instrument and the insertion part of the second medical instrument are inserted, and is configured to guide the insertion part of the first medical instrument and the insertion part of the second medical instrument into a body cavity, wherein
the outer tube comprises:
a cylindrical outer tube body into which the insertion part of the first medical instrument and the insertion part of the second medical instrument are inserted;
a first entry port provided at a proximal end part of the outer tube body;
a second entry port provided at the proximal end part of the outer tube body;
a first sealing member which is provided at the first entry port and configured to slidably seal the insertion part of the first medical instrument;
a second sealing member which is provided at the second entry port and configured to slidably seal the insertion part of the second medical instrument;
a first exit port provided at a distal end part of the outer tube body;
a second exit port provided at the distal end part of the outer tube body;
a movable object which is arranged in the outer tube body and is configured to be movable in the outer tube body in an axial direction;
a first holding part which is provided at the movable object and configured to hold the insertion part of the first medical instrument inserted into the outer tube body; and
a second holding part which is provided at the movable object and configured to hold the insertion part of the second medical instrument inserted into the outer tube body,
the insertion part of the first medical instrument comprises:
a part which is to be held by the first holding part and has a first diameter A1; and
a part which is disposed closer to a proximal end than the part having the first diameter A1, and is configured to maintain hermeticity with the first sealing member, and has a second diameter A2 being larger than the first diameter A1, and
interlocked movement of the first medical instrument and the second medical instrument has play by one of the first holding part and the second holding part.

22. The surgical device according to claim 21, wherein the first medical instrument is an endoscope.

23. An outer tube into which an insertion part of a first medical instrument and an insertion part of a second medical instrument are inserted, and is configured to guide the insertion part of the first medical instrument and the insertion part of the second medical instrument into a body cavity, the outer tube comprising:
a cylindrical outer tube body into which the insertion part of the first medical instrument and the insertion part of the second medical instrument are inserted;
a first entry port provided at a proximal end part of the outer tube body;
a second entry port provided at the proximal end part of the outer tube body;
a first sealing member which is provided at the first entry port and configured to slidably seal the insertion part of the first medical instrument;
a second sealing member which is provided at the second entry port and configured to slidably seal the insertion part of the second medical instrument;
a first exit port provided at a distal end part of the outer tube body;
a second exit port provided at the distal end part of the outer tube body;
a movable object which is arranged in the outer tube body and configured to be movable in the outer tube body in an axial direction;
a first holding part which is provided at the movable object and configured to hold the insertion part of the first medical instrument inserted into the outer tube body; and
a second holding part which is provided at the movable object and configured to hold the insertion part of the second medical instrument inserted into the outer tube body, wherein
the insertion part of the first medical instrument comprises:
a part which is to be held by the first holding part and has a first diameter A1; and
a part which is disposed closer to a proximal end than the part having the first diameter A1, and is configured to maintain hermeticity with the first sealing member, and has a second diameter A2 larger than the first diameter A1, and wherein
interlocked movement of the first medical instrument and the second medical instrument has play by one of the first holding part and the second holding part.

24. The outer tube according to claim 23, wherein the first medical instrument is an endoscope.

\* \* \* \* \*